United States Patent [19]
Li et al.

[11] Patent Number: 6,103,511
[45] Date of Patent: Aug. 15, 2000

[54] LICHENASE AND CODING SEQUENCES

[75] Inventors: Xin-Liang Li; Lars G. Ljungdahl, both of Athens; Huizhong Chen, Lawrenceville, all of Ga.

[73] Assignee: University of Georgia Research Foundation, Inc., Athens, Ga.

[21] Appl. No.: 09/286,690

[22] Filed: Apr. 5, 1999

Related U.S. Application Data

[63] Continuation-in-part of application No. PCT/US97/17811, Oct. 3, 1997.

[60] Provisional application No. 60/027,882, Oct. 4, 1996.

[51] Int. Cl.[7] .............................. C12N 9/00; C12N 9/42; C12N 9/58
[52] U.S. Cl. .......................... 435/209; 435/195; 435/223; 435/252.3; 435/320.1; 536/23.2
[58] Field of Search ............................. 435/254.21, 200, 435/69.1, 195, 209, 252.3, 325, 320.1; 536/23.2, 23.4, 23.74

[56] References Cited

FOREIGN PATENT DOCUMENTS

| 01067181 | 3/1989 | Japan | C12N 1/20 |
|---|---|---|---|
| 96/36701 | 11/1996 | WIPO | C12N 9/24 |

OTHER PUBLICATIONS

Borneman et al. (1989) "Fermentation Products and Plant Cell Wall–Degrading Enzymes Produced by Monocentric and Polycentric Anaerobic Ruminal Fungi" *Applied and Environmental Microbiology* 55:1066–1073.

Borriss et al. (1990) "Structure of the Beta–1,3–1,4–Glucanase Gene of *Bacillus macerans*: Homologies to Other Beta–Glucanases" *Mol. Gen. Genet.* 222:278–283.

Buliga et al. (1986) "The Sequence Statistics and Solution Conformation of a Barley (1→3,1→4)–β–D–Glucan" *Carbohydrate Research* 157:139–156.

Chen et al. (1997) "Sequencing of a 1,3–1,4–β–D–Glucanase (Lichenase) from the Anaerobic Fungus Orpinomyces Strain PC–2: Properties of the Enzyme Expresses in *Escherichia coli* and Evidence That the Gene Has a Bacterial Origin" *Journal of Bacteriology* 179:6028–6034.

Chen et al. (1995) "A Cyclophilin from the Polycentric Anaerobic Rumen Fungus Orpinomyces sp. Strain PC–2 is Highly Homologous to Vertebrate Cyclophilin B" *Proc. Natl. Acad. Sci. USA* 92:2587–2591.

Chen et al. (1992) "Molecular Cloning and Expression of *Bacillus subtilis* bg1S Gene in *Saccharomyces cerevisiae*" *Current Microbiology* 25:279–282.

Cornelis et al. (1982) "Cloning and Expression of a *Bacillus coagulans* Amylase Gene in *Escherichia coli*" *Mol. Gen. Genet.* 186:507–511.

Erfle et al. (1988) "Purification and Properties of a 1,3–1,4–β–D–Glucanase (Lichenase, 1,3–1,4–β–D–Glucan 4–Glucanohydrolase, EC 3.2.1.73) from *Bacteroides succinogenes* Cloned in *Escherichia coli*" *Biochem. J.* 255:833–841.

Fanutti et al. (1995) "The Conserved Noncatalytic 40–Residue Sequence in Cellulases and Hemicellulases from Anaerobic Fungi Functions as a Protein Docking Domain" *The Journal of Biological Chemistry* 270:29314–29322.

Fincher et al. (1986) "Primary Structure of the (1→3,1→4)–β–D–Glucan 4–Glucohydrolase from Barley Aleurone" *Proc. Natl. Acad. Sci. USA* 83:2081–2085.

Flint et al. (1993) "A Bifunctional Enzyme, with Separate Xylanase and β(1,3–1,4)–Glucanase Domains, Encoded by the xynD Gene of *Ruminococcus flavefaciens*" *Journal of Bacteriology* 175:2943–2951.

Gilbert et al. (1992) "Homologous Catalytic Domains in a Rumen Fungal Xylanase: Evidence for Gene Duplication and Prokaryotic Origin" *Molecular Microbiology* 6:2065–2072.

Henrissat and Bairoch (1993) "New Families in the Classification of Glycosyl Hydrolases Based on Amino Acid Sequence Similarities" *Biochem. J.* 293:781–788.

Huber and Nevins (1977) "Preparation and Properties of a β–D–Glucanase for the Specific Hydrolysis of β–D–Glucans" *Plant Physiol.* 60:300–304.

Lloberas et al. (1991) "Molecular Cloning, Expression and Nucleotide Sequence of the Endo–β–1,3–1,4–D–Glucanase Gene from *Bacillus licheniformis*" *Eur. J. Biochem.* 197:337–343.

Neu and Heppel (1965) "The Release of Enzymes from *Escherichia coli* by Osmotic Shock and During the Formation of Spheroplasts" *The Journal of Biological Chemistry* 240:3685–3692.

Pitson et al. (1993) "Noncellulolytic Fungal β–Glucanases: Their Physiology and Regulation" *Enzyme and Microbial Technology* 15:178–192.

Teather and Erfle (1990) "DNA Sequence of a *Fibrobacter succinogenes* Mixed–Linkage β–Glucanase (1,3–1,4–β–D–Glucan 4–Glucanohydrolase) Gene" *Journal of Bacteriology* 172:3837–3841.

Zhou et al. (1994) "Intronless celB from the Anaerobic Fungus *Neocallimastix patriciarum* Encodes a Modular Family A Endoglucanase" *Biochem. J.* 297:359–364.

*Primary Examiner*—Rebecca E. Prouty
*Assistant Examiner*—Maniunath N Rao
*Attorney, Agent, or Firm*—Greenlee Winner and Sullivan PC

[57] ABSTRACT

The present invention provides a fungal lichenase, i.e., an endo-1,3-1,4-β-D-glucanohydrolase, its coding sequence, recombinant DNA molecules comprising the lichenase coding sequences, recombinant host cells and methods for producing same. The present lichenase is from Orpinomyces PC-2.

13 Claims, 8 Drawing Sheets

1 2 3 4

1    2    3

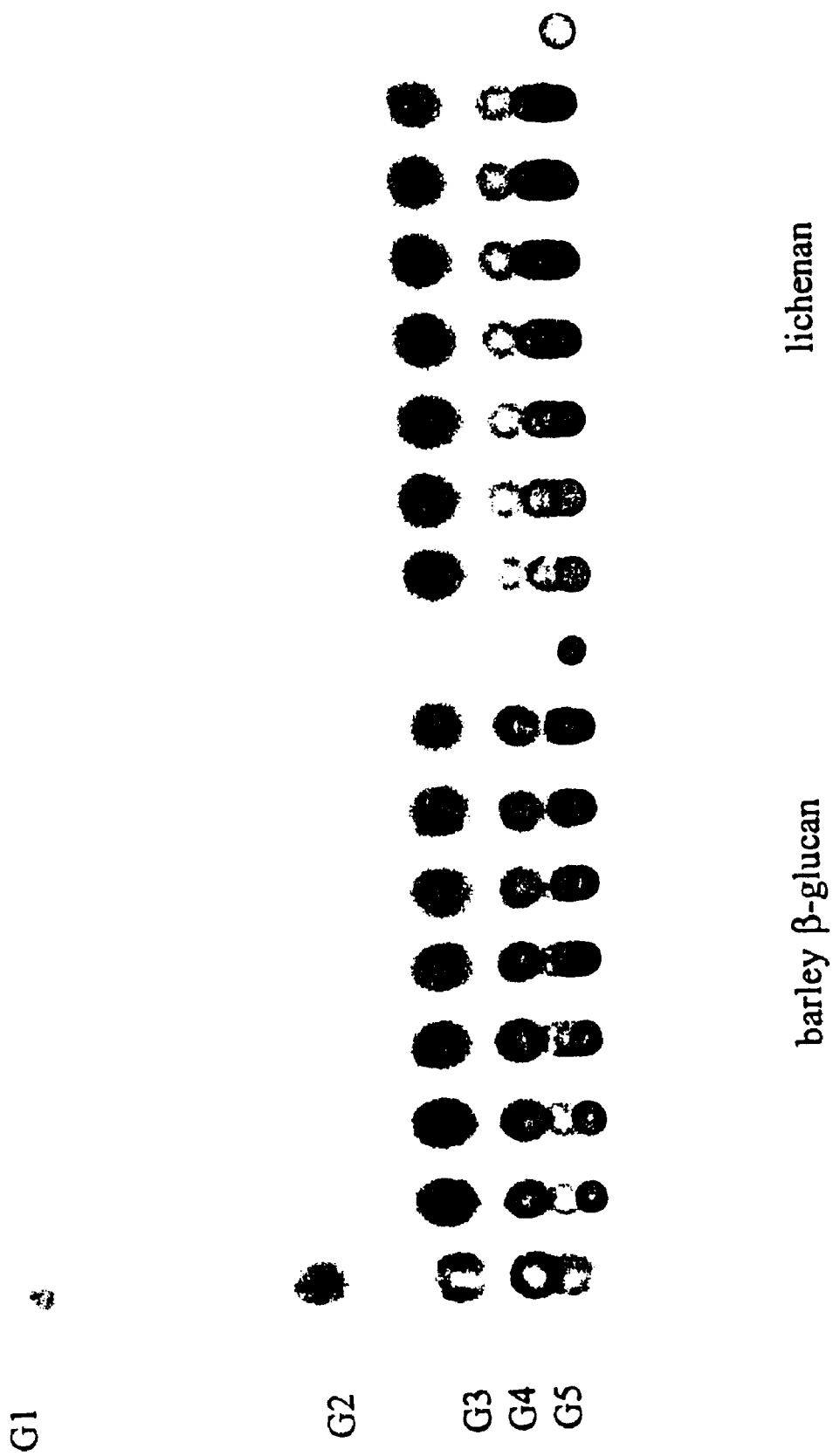

FIG. 8C CMC cellulose zymogram
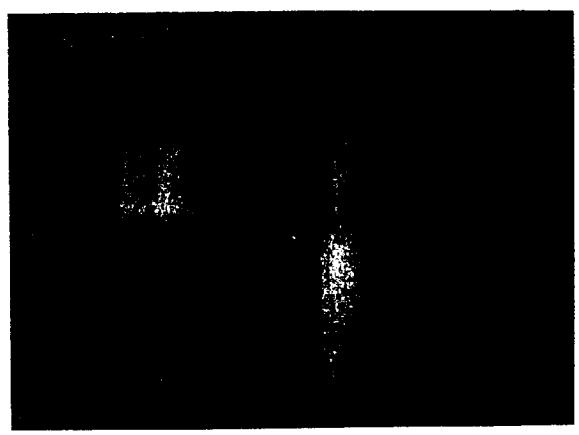
FIG. 8B Lichenan zymogram
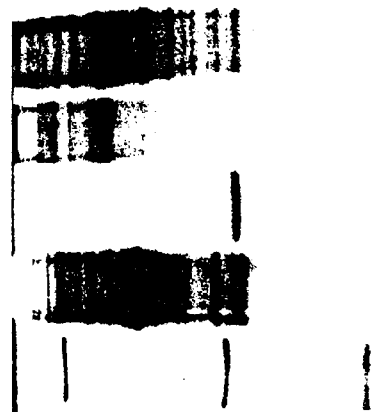
FIG. 8A Protein staining

LICHENASE AND CODING SEQUENCES

CROSS REFERENCE TO RELATED APPLICATIONS

The present application is a continuation-in-part of International Patent Application PCT/US97/17811, filed Oct. 3, 1997, which claims priority from United States Provisional Application No. 60/027,882, filed Oct. 4, 1996.

STATEMENT REGARDING FEDERAL RESEARCH SUPPORT

This invention was made, at least in part, with funding from the United States Department of Energy. Accordingly, the United States Govermnent has certain rights in this invention.

BACKGROUND OF THE INVENTION

The present invention relates to polysaccharide-degrading enzymes, especially to the enzymes, in particular, to a lichenase enzyme which is capable of degrading (1,3-1,4)-β-glucans and sequences encoding lichenase enzymes.

Hemicellulose (non-cellulosic polysaccharides including glucans, mannans and xylan) is the major constituents of plant cell walls. The mixed-linked 1,3-1,4-β-glucans form the major part of cell walls of cereals like oat and barley. β-Glucans consist of glucose units jointed by β-1,4 and β-1,3 linkages, and include lichenan and barley β-glucan. β-Glucan accounts for up to 70% of the cell wall in barley endosperm (Guliga and Brant, 1986).

Endo-1,3-1,4-β-D-glucanohydrolase (1,3-1,4-β-glucanase, lichenase) cleaves β-1,4 linkages adjacent to β-1,3 in glucans yielding chiefly cellobiosyltriose and cellotriosyltetraose (Fleming and Kawami, 1977; Anderson and Stone, 1975). β-Glucanase is especially interesting to the brewing industry because β-glucans cause problems in filtration processes (Godfrey, 1983). β-glucanase also has application in the poultry industry; it has been added to broiler chick feedstuffs to improve digestibility (White et al., 1983). β-Glucanases have been cloned from several Bacillus species, including *Bacillus subtilis* (Murphy et al., 1984), *B. amyloliquefaciens* (Hofemeister et al., 1986), *B. macerans* (Borriss et al 1990), *B. licheniformis* (Lloberas et al., 1991), *B. brevis* (Louw et al., 1991), *B. polymyxa* (Gosalbes et al., 1991), and from other genera, including *Clostridium thermocellum* (Schimming et al., 1992; Zverlov et al., 1992), *Fibrobacter succinogenes* (Teather and Erfle, 1990), *Ruminococcus flavefaciens* (Flint et al., 1993), *Rhizobium meliloti* (Berker et al., 1993, and *Cellvibrio mixtus* (Sakellaris et al., 1993). A cDNA clone encoding barley 1-glucanase has been isolated and sequenced from germinating barley (Fincher et al., 1986).

Unlike endo-1,4-β-D-cellulases which are widely distributed in various organisms, 1,3-1,4-β-D-glucanases are known to be produced only by plants and certain bacteria (Borriss et al., 1990; Fincher et al., 1986). No fungal 1,3-1,4-β-glucanases which lack the ability to degrade 1,3-(1,4)-glucans are believed to have been discovered prior to the present invention.

Obligately anaerobic fungi are part of the natural microflora of the alimentary tract of many herbivorous mammals (Orpin and Joblin, 1988). Since the first strictly anaerobic and filamentous fungus *Neocallimastix frontallis* was isolated in 1975 from the rumen of a sheep (Orpin, 1975), at least thirteen different anaerobic fungi have been isolated from ruminant and nonruminant herbivores (Chen et al., 1995a). Anaerobic fungi are divided into two groups based on morphology. One is monocentric, and it includes Neocallimastix (Orpin, 1975), Caecomyces (Wubah and Fuller, 1991), and Piromyces species (Barr et al., (1989) *Can. J Botany* 67:2815–2824); the other is polycentric and it contains Orpinomyces (Barr et al., (1989) supra), Anaeromyces (Breton et al., 1990), and Ruminomyces (Ho and Bauchop, 1990). The anaerobic fungi produce a variety of enzymes that degrade plant materials ingested by the host animals (Borneman et al., 1989). The physical association with the lignocellulosic tissues of plant fragments, and the ability to penetrate and weaken the plant tissue in vivo (Akin et al., 1983) suggest that the fungi are involved in degradation of digesture and that they play an important role in the rumen ecosystem. Several cellulases and xylanases have been cloned and sequenced from both monocentric *Neocallimastix patriciarum* (Gilbert et al., 1992; Zhou et al., 1994; Black et al., (1994) *Biochem. J* 299:381–387; Denman et al., (1996) *Appl. Envir. Microbiol* 62:1889–1896; Piromyces sp. (Fanutti et al., 1995) and polycentric Orpinomyces PC-2. A mannanase was cloned and sequenced from Piromyces sp. (Fanutti et al., 1995).

SUMMARY OF THE INVENTION

The present invention provides a substantially purified lichenase. As used herein, a lichenase is an enzyme which hydrolyzes the β-1,4-glucan bonds adjacent to β1,3-linked glucan bonds, but does not cleave β-1,4-linked glucans. Substrates for lichenase include, without limitation, lichenan and barley β-glucan. As specifically exemplified, the lichenase is selected from the group consisting of that naturally produced by Orpinomyces PC2 (SEQ ID NO:2, amino acids 1 to 216) and that recombinantly produced, for example, in *Escherichia coli* (SEQ ID NO:2, amino acids -8 to 216). The complete amino acid sequence of the exemplified lichenase, including the signal sequence, is given in SEQ ID NO:2, amino acids -29 to 216.

It is a further object of the invention to provide a nucleotide sequence encoding a mature lichenase enzyme from Orpinomyces, where that sequence has at least about 80% sequence identity with the exemplified coding sequence (nucleotides 209 to 860 of SEQ ID NO:1) and encodes a lichenase enzyme having the same enzymatic specificity as the exemplified lichenase. Additional objects of the invention are nucleotide sequences which encode a lichenase enzyme of the disclosed specificity and having an amino acid sequence as given in SEQ ID NO:2, amino acid 1 to amino acid 216 or as given in SEQ ID NO:2, from amino acid -8 to amino acid 216 or as given in SEQ ID NO:2 from -29 to 216, for a lichenase with signal sequence. Variations from the specifically exemplified sequence are permitted, to the extent that the functionality of the enzyme is not changed.

Specifically exemplified embodiments of the Orpinomyces PC2 coding sequences for a mature natural lichenase is as given in SEQ ID NO: 1, nucleotides 209–860; for the recombinantly expressed lichenase, SEQ ID NO:1, nucleotides 185–860, and for the complete coding sequence including the signal peptide, SEQ ID NO:1, nucleotides 123–860, and sequences with at least about 70% homology to the recited Sequences. Synonymous codings are within the scope of the present invention, and are well within the grasp of the ordinary skilled artisan without the expense of undue experimentation, given the teachings of the present disclosure taken with what is well known to the art.

It is a further object of the present invention to provide non-naturally occurring 1=5- recombinant DNA molecules which direct the expression of a lichenase protein of the present invention. Where expression and secretion is desired, the complete coding sequence (SEQ ID NO:1, nucleotides 123–860) is operably linked downstream of promoter sequences appropriate to the recombinant host cell in which expression is desired. If it is preferred that the expressed lichenase protein be intracellular, then the coding sequence for lichenase (either as given in SEQ ID NO:1, nucleotides 186–860 or as given in SEQ ID NO:1, nucleotides 210–860) is joined immediately downstream of a translation start signal (ATG) and operably linked downstream of a promoter appropriate to the host cell of choice. Recombinant cells which express lichenase, also an object of the present invention, are cultured under conditions suitable for the expression of the lichenase coding sequence. Where an inducible promoter is used to control the expression of the lichenase coding sequence, the skilled artisan understands that it is desirable or essential, depending on the inducible promoter, to add the cognate inducer to the culture to effect gene expression. Substitution of alternative signal peptide coding sequences is also within the skill of the skilled artisan.

A further object of the present invention is to provide a method for the expression of a lichenase protein of the present invention. This method includes the step of producing a non-naturally occurring recombinant DNA molecule as described hereinabove, with the lichenase coding sequence operably linked to transcriptional and translational control sequences suitable for the host cell of choice, said combination being incorporated within a vector plasmid or virus suitable for the chosen host cell, introducing that recombinant DNA molecule into the host cell to produce a recombinant host cell, and culturing the recombinant host cells under conditions suitable for expression of the lichenase coding sequence. Substantially pure lichenase can be purified from cell-free medium of such cultures using the methods provided herein.

It is a further object of the present invention to provide a substantially pure lichenase, said lichenase having the ability to cleave β-1,4 glucan bonds adjacent to β-1,3 glucan bonds, but having no hydrolytic activity for β-1,4 glucans. As specifically exemplified, the lichenase expressed by Orpinomyces PC2 has an extracellular (secreted) enzyme having a molecular weight of about 26 kDa, while the recombinant enzyme expressed and secreted by *Escherichia coli* has an apparent molecular weight of about 27 kDa. The lichenase of the present invention has no apparent activity when assayed with carboxymethylcellulose as substrate.

BRIEF DESCRIPTION OF THE DRAWINGS

FIG. 7 is a photograph of a thin layer chromatogram of the products of barley β-glucan and lichenan incubated with Orpinomyces lichenase.

FIG. 8A shows the protein staining profile for low molecular weight standards (lane 1), crude recombinant *E. coli* cell extract (lane 2), purified recombinant LICA (lane 3), supernatant from Orpinomyces PC2 grown on CBG (lane 4) and supernatant from Neocallimastix EB188 grown on CBG (lane 5). FIG. 8B is a lichenan zymogram and FIG. 8C is a CMC cellulose zymogram. Lanes are as in FIG. 8A.

DETAILED DESCRIPTION OF THE INVENTION

Figure 1:
FIG. 1 shows protein staining patterns for crude enzyme sample (lane 1) and purified enzyme (lane 2) and the lichenase activity patterns for the crude enzyme sample (lane 3) and purified enzyme (lane 4) using lichenase as the substrate.

As used herein, lichenase is used synonymously with endo-β-(1-3,1-4)-D-glucanase; the enzyme code assigned to enzymes having this activity is EC 3.2.1.73.

The gene and cDNA encoding the lichenase of the present invention is called licA. As specifically exemplified, the mature licA gene product (LICA) has an amino acid sequence as given in SEQ ID NO:2, amino acids 1–216 as expressed in Orpinomyces PC2, or a functionally equivalent amino acid sequence, for example, as given in SEQ ID NO:2, amino acids −8 to 216, or −29 to 216. Also encompassed by the present invention are lichenases with about 70% amino acid sequence identity to any of the foregoing sequences. These functionally equivalent sequences differ in the proteolytic cleavage site for the removal of the signal peptide.

The lichenase of the present invention is distinguished from prior art lichenases from rumen bacteria in that there are no repeated oligopeptide sequence motifs in the present lichenase. Without wishing to be bound by theory, it is proposed that the lack of the repeated motifs contributes to the efficient expression and secretion, with functionally correct signal peptide processing in the *Escherichia coli* recombinant host cells.

The lichenase proteins of the present invention is useful for treatment of animal grain-containing feeds to improve nutrient availability and for treatment of grain (e.g. barley or wheat) in the brewing and fermentation industries to increase carbon substrate availability and to maximize production of desired products. The lichenase coding sequences of the present invention are useful to direct the recombinant expression (in Orpinomyces or in other host cells, including, but not limited to, *Escherichia coli, Bacillus subtilis, Aspergillus nidulans, Aspergillus niger, Saccharomyces cerevisiae,* and *Pichia pastoris*).

A cDNA expression library in ZAPII using MRNA isolated from Orpinomyces sp. strain PC-2 cells cultivated with Avicel and oat spelt xylan as carbon source was screened for clones with β-glucanase activity on lichenan plates. Initially, 15 positive plaques were identified after screening 2×10$^4$ plaques from the library. Eight of them were randomly choses for further enrichment and purification. The remaining lichenase-positive clones were not further studied. After secondary screening, the recombinant lambda clones were converted to pBluescript clones. Then these eight clones were tested for CMCase (carboxymethylcellulose-degrading activity) and lichenase activities after culturing them in LB-ampicillin medium. Three of them showed only lichenase activity without detectable CMCase activity; these clones contain the licA coding sequence. Four of them exhibited both lichenase and CMCase activities, and these later were further confirmed as cellulase-positive clones.

Analysis of the lichenase producer clones by restriction mapping revealed that they had similar restriction patterns (inserts of 0.9, 1.0, and 1.7 kbp, respectively). Sequencing of both ends of the inserts showed that they were transcripts from the same gene (licA) differing in length at their 3' ends.

The complete nucleotide sequence of licA derived from pLIC6 (1.0 kbp) was determined (Table 4, SEQ ID NO:1). The whole sequence was 971 bp with a G-C content of 28%, and it contained an open reading frame (ORF) encoding a polypeptide of 245 amino acids with a calculated $M_r$ value of 27,929 (See SEQ ID NO:2). A typical 18-mer poly(A) tail was found at its 3' end. The putative start codon (ATG) for licA was identified because there were stop codons in all three reading frames preceding the ORF, there was no ATG codon upstream of the identified ORF, and a typical signal peptide occurred at the N-terminus of the ORF. In addition, zymogram analysis and N-terminal sequencing of the purified LICA enzyme from the recombinant $E.$ $coli$ supernatant and partially purified native enzyme from Orpinomyces PC-2 further confirmed this assignment. Only one potential N-glycosylation site ($Asn^{34}$-Gly-$Ser^{36}$) was present near the N-terminus of the mature enzyme; the enzyme may not be glycosylated.

The G+C content of the ORF of licA was 35.5% while that of the 5' and 3' non-coding sequences was extremely low (4.3%). The codon usage for licA was similar to that observed for other Orpinomyces PC-2 cellulase and xylanase genes. 21 codons were not utilized, and there was a marked preference for a T in the third position (53% of all codons contained T in the third position).

mRNAs of anaerobic fungi do not contain a typical $E.$ $coli$ Shine-Dalgarno-like sequence for translation initiation. However, presumably the sequence AGA, 10 bp upstream of the ATG start codon, acts as a weak ribosome-binding sequence in $E.$ $coli$. This sequence was also found in a xylanase gene (xyn,) from $N.$ $patriciarum$ (Gilbert et al., 1992).

The deduced amino acid sequence of the protein LICA was compared with other protein sequences in the SWISS PROT and GP data banks. A number of β-glucanases from mesophilic and thermophilic bacteria, including anaerobic rumen bacteria, with some identity to LICA were found. Greater than 50% identity was found with β-glucanases from certain Bacillus strains, $Clostridium$ $thermocellum$, and the carboxy-terminal lichenase domain of the xylD gene of the anaerobic rumen bacterium $R.$ $flavefaciens$. LICA has 30.6% amino acid identity with β-glucanase from $Fibrobacter$ $succinogenes$ (Table 1). In contrast, limited sequence homology was found upon comparison with barley β-glucanase.

Some of the homologous sequences were aligned with LICA sequence (Table 5). This alignment revealed that the similarity between these β-glucanases is stronger in the central and C-terminal parts of the proteins. The motif DEIDI (SEQ ID NO:6), which is located in the active site cleft in lichenase from $Bacillus$ $licheniformis$ $formis$ (Juncosa et al., 1994), was conserved in the LICA sequence (133–137 position). According to the classification of Henrissat and Bairoch (1993), LICA should be placed in Glycosyl Hydrolase Family 16, which includes most bacterial lichenases.

In order to study the expression and the distribution of the β-glucanase synthesized in $E.$ $coli$ harboring pLIC6, extracellular, periplasmic and cellular fractions were isolated according to the method described by Cornelis et al. (1982). A major part of the total activity was found in the extracellular fraction, with significant periplasmic activity. These two fractions contained greater than 90% of the expressed enzyme activity in $E.$ $coli$. β-Galactosidase and alkaline phosphatase were used as cytoplasmic and periplasmic markers, respectively. Additionally, the secreted enzyme encoded by clone pLIC6 was visualized by the zymogram technique involving renaturation of enzyme activity following separation by sodium dodecyl sulfate (SDS)-polyacrylamide gel electrophoresis (FIG. 1). The results show that a strong polypeptide band detected at 27 kDa exhibited only lichenase but not CMCase activity.

Taken with results for the N-terminal sequence of the mature protein, these results indicate that the export mechanism of $E.$ $coli$ accepts export signals from the anaerobic fungus Orpinomyces lichenase, correctly processes the protein and transports it to the periplasmic space. Similar results have been reported for expression of bacterial extracellular lichenase genes cloned in $E.$ $coli$ (Lloberas, 1991; Borriss et al. 1990). By contrast, the xylanase, the cellulase and the mannanase from the fungus N. partricerum expressed in $E.$ $coli$ were found predominantly in cell-free extracts, indicating that these enzymes were not effectively secreted by $E.$ $coli$ (Gilbert et al, 1992; Zhou et al., 1994, Fanutti et al., 1995).

A summary of the purification of the recombinant LICA from the supernatant of the $E.$ $coli$ culture is given in Table 2. The enzyme was purified about 24-fold, with a yield of about 43.5%. Based on calculations of the specific lichenase activity of the purified LICA and the recovery of the enzyme, the recombinant LICA protein constituted about 4% of the secreted protein in the recombinant $E.$ $coli$ culture. Considering that $E.$ $coli$ XL1 is not considered a superb expression host for recombinant proteins, the surprisingly large amount of recombinant LICA detected in the culture supernatant indicates that the signal sequence of LICA is very effectively processed in $E.$ $coli$. Using a similar purification strategy and zymogram analysis to monitor lichenase, the native lichenase from the supernatant of Orpinomyces PC-2 culture was also partially purified.

Analysis of the amino acid sequence of the N-terminus of the recombinant LICA isolated from the supernatant of $E.$ $coli$ culture indicated that the recombinant protein is processed in $E.$ $coli$, with a 21 -amino acid signal sequence being removed to give a mature active enzyme of 224 amino acids (22 N-terminal residues if the LICA exactly matched the deduced protein sequence). The presumptive 21-amino-acid signal sequence deduced from the DNA sequence contains all of the features normally associated with a signal sequence for secretion (Von Heijne, 1988), including a positively charged lysine (−20) terminal n region and a strongly hydrophobic h region from amino acid residues −18 through −6 (10 out of 13 are hydrophobic; amino acid positions are given relative to the first residue of the mature peptide). The c region of the signal peptide conforms to the "(−3, −1) rule", with small, uncharged threonine and alanine residue at positions −3 and −1 relative to the cleavage site, which is typical for a peptide cleaved by signal peptidase I in $E.$ $coli$ see SEQ ID No:2.

The partially purified native lichenase from supernatant of Orpinomyces PC-2 culture was subjected to N-terminal sequence analysis. The enzyme had a Mr of 26,000 and an N-terminal sequence of GTAWNGLHDVMD, (SEQ ID NO:3) which, with the exception of one amino acid, matched the corresponding amino acid sequence deduced from the DNA sequence. Thus, a 29-amino acid signal sequence was removed to give a natural mature enzyme of 216 amino acids (Table 4). These results indicate that there are differences in the substrate specificities of the prokaryotic *E. coli* and eukaryotic (anaerobic fungus) signal peptidases. Normally, proline is conspicuously absent from −3 to +1 regions of prokaryotic signal peptides, but it is not usual to have proline at the corresponding region of eukaryotic signal peptide (Von Heijne, 1986). Another reason for the lichenase N-terminal signal sequence being processed differently may come from "the Charge-Block Effect". A region encompassing the first 10–20 resides of the mature protein is also critical for the initiation of membrane translocation in *E. coli* (Anderson and von Heijne, 1991). This region normally contains few positively charged amino acids; hence, the introduction of only one or two extra positively charged amino acids can dramatically affect secretion (Li et al., 1988). With much higher numbers of charged residues, a similar blocking effect can be observed in eukaryotic secreted proteins (Kohara et al., 1991). The first 20 amino acid residues of the mature recombinant lichenase contain only one positively charged amino acid (histidine); this makes the processed enzyme effectively secreted. If the cleavage site of the lichenase processed in *E. coli* was the same as in the fungus, the mature recombinant lichenase would be difficult to export from *E. coli*, simply because the N-terminal region of the mature chain carries too many positively charged amino acids (3 out of 20 animo acid residues).

Figure 2:
FIG. 2 is a photograph of crude (lane 2) and purified recombinant lichenase (lane 3) from the extracellular medium of the *E coli* culture producing the lichenase. Lane 1 contains the low molecular weight standards.
Figure 3:
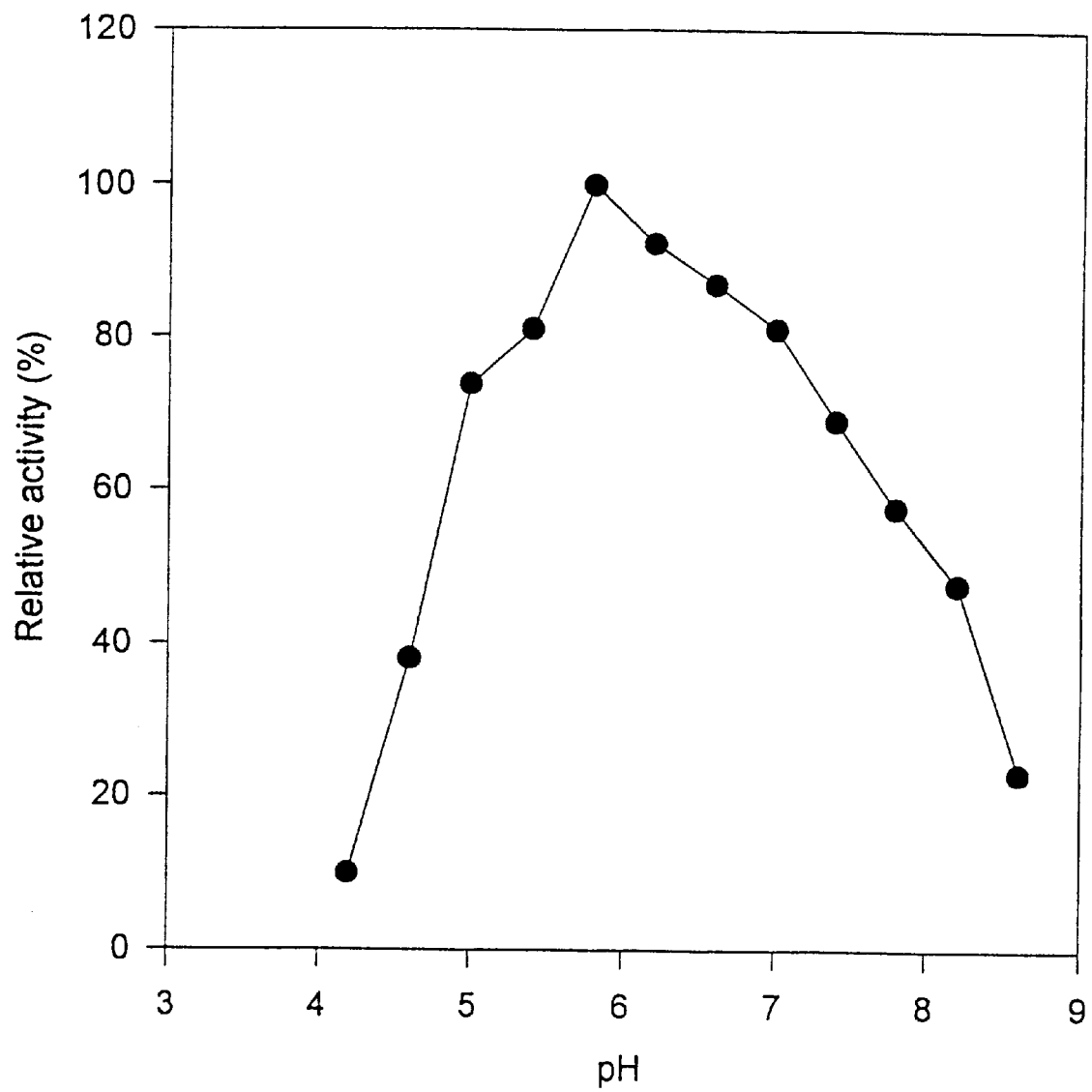
FIG. 3 shows the effects of pH on the activity of the Orpinomyces lichenase. Maximal activity on the curve is defined as 100%.
Figure 4:
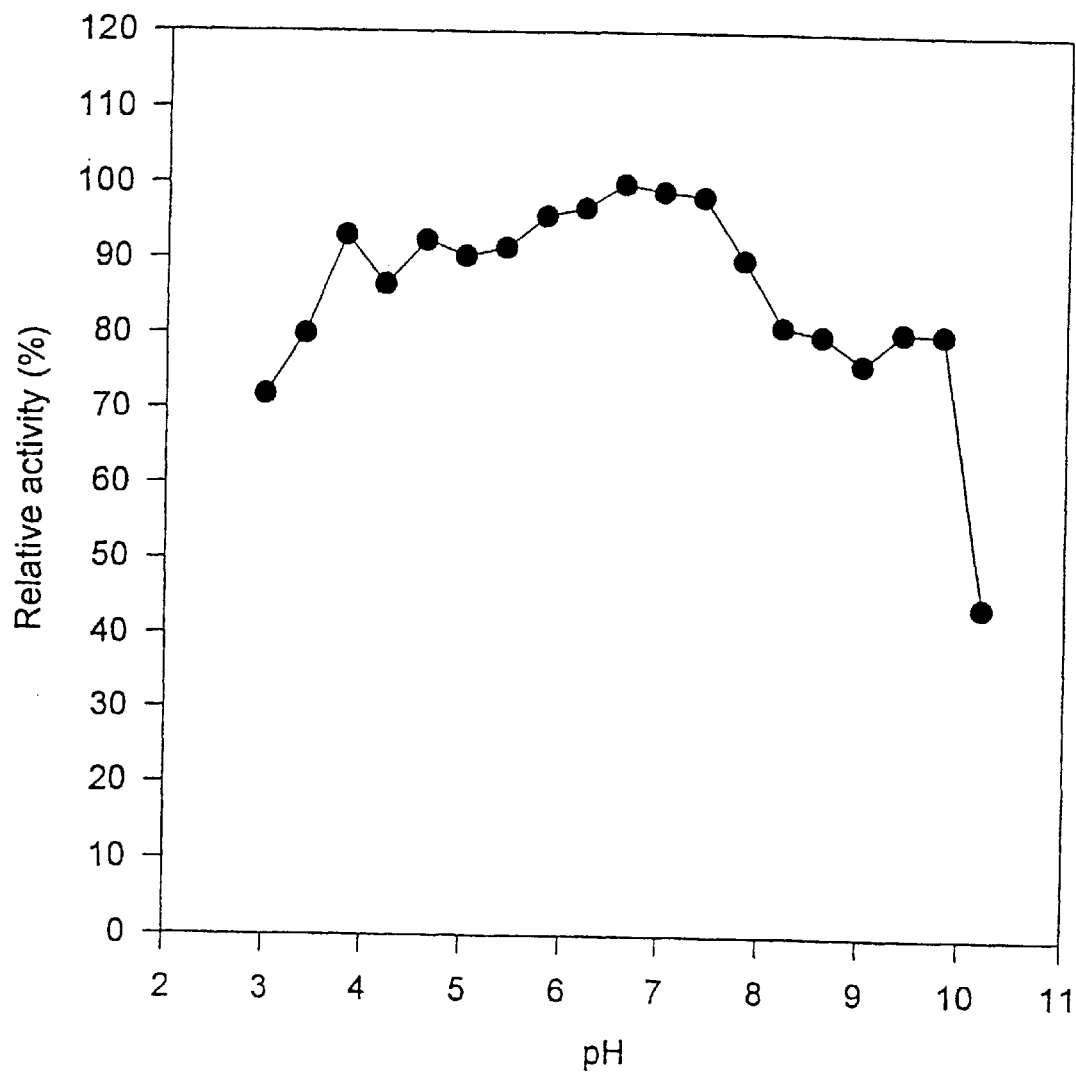
FIG. 4 illustrates the pH stability of the Orpinomyces lichenase.
Figure 5:
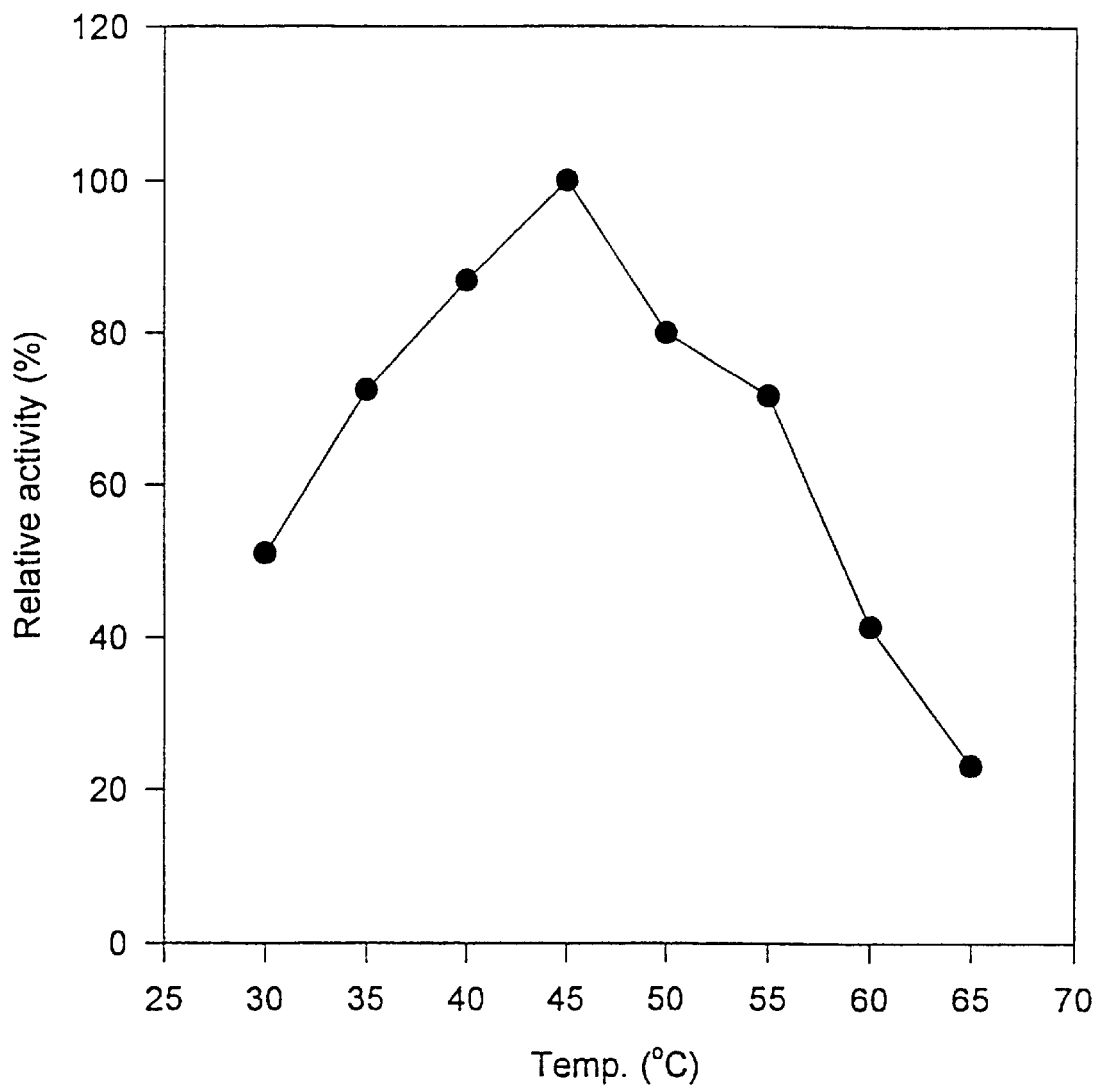
FIG. 5 shows the effect of temperature on Orpinomyces lichenase activity. Maximal activity is defined as 100%.
Figure 6:
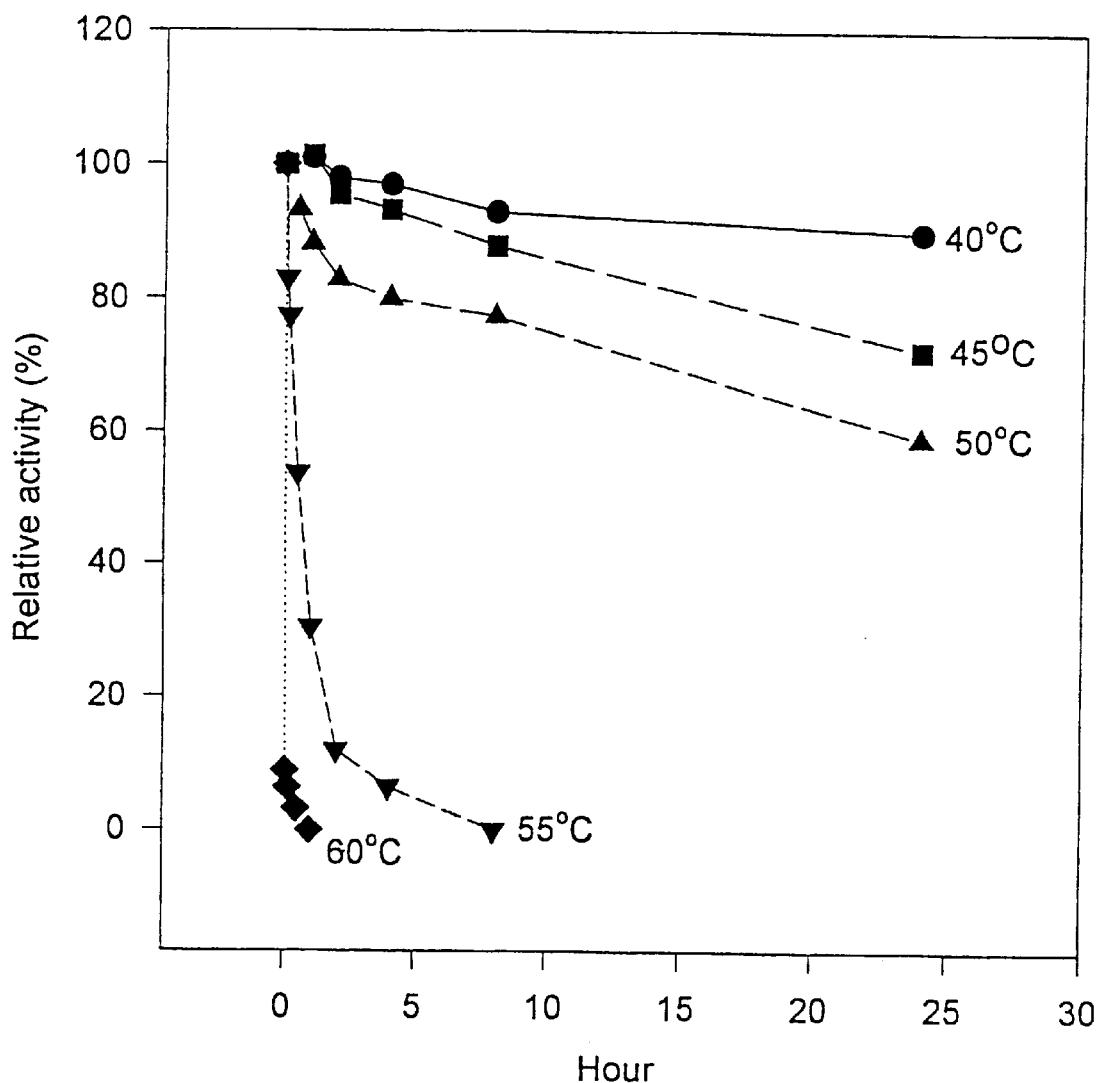
FIG. 6 shows thermostability profiles for Orpinomyces lichenase at selected temperatures.

The purified recombinant lichenase appeared as single band with an apparent molecular mass of 27 kDa on SDS-PAGE (FIG. 2), which is consistent with the deduced molecular mass of the mature LICA (25.7 kDa) after removal of a signal peptide of 21 animo acid residues. The lichenase activity of the enzyme was measured from pH 4.2 to 8.6 using lichenan as substrate. A typical pH profile was obtained (FIG. 3), with a broad pH optimum from pH 5.8–6.2, with approximately 80% of maximum activity at pH 5.4 and pH 7.0. The enzyme was stable for at least 24 h between pH 3.4 and 9.8 at 4° C. (FIG. 4). The lichenase activity was measured in 50 mM sodium citrate at pH 6.0 from 30 to 65° C. Maximum activity was observed at 45° C. (FIG. 5). The enzyme exhibited at least 70% of its optimal activity over the range 35–55° C., and its activity decreased rapidly above 55° C. Thermal stability was investigated by incubating the enzyme, up to 24 h, at different temperatures (FIG. 6). Almost no activity loss was observed at 40° C. with incubation in the above buffer for 24 h. 72% and 59% of the enzyme activity was retained after 24 h incubation at 45° C. and 50° C., respectively. Inactivation occurred at 55° C. with only 30% of the enzyme activity remaining after 1 h.

The enzymatic activities of the recombinant lichenase were assayed using lichenan, barley-β-glucan, laminarin, pachyman, CMC, acid swollen cellulose, puslutan and other =polysaccharides and glycosides as substrates and analyzed by the dinitrosalicylic acid (DNS) method. The enzyme was specific for polysaccharides with mixed 1,3-1,4-β-D-linkages (lichenan and barley β-glucan) and did not hydrolyze the other substrates tested (Table 3). $K_m$ and $V_{max}$ values at 40° C. were obtained from Lineweaver-Burk plots. $K_m$ values of the enzyme towards lichenan and barley-β-glucan were 0.75% (w/v) and 0.91% (w/v) and $V_{max}$ values were 3,786 and 5,314 U/mg protein, respectively.

The nature of products formed during the action of the purified recombinant lichenase on lichenan and barley-β-glucan was studied using silica gel thin layer chromatography (TLC, FIG. 7). In extended incubation with both substrates, the reactions proceeded to apparent completion. With lichenan as substrate, the major product was a triose which was migrated on TLC just slightly ahead of cellotriose, and was considered to be 3-O-β-cellobiosyl-D-glucose (Huber and Nevin, 1977; Erfle et al., 1988). Minor products included pentose (3-O-β-cellotetraosyl-D-glucose) and tetraose (3-O-β-cellotriosyl-D-glucose) which migrated on TLC a little ahead of cellopentose and cellotriose. An additional minor component was a biose (laminobiose), which migrated ahead of cellobiose. Barley β-glucan treated in the same manner gave distinctly different profiles which reflected the structural differences between lichenan and barley β-glucan (Buliga et al., 1986). The major products from barley β-glucan hydrolysis were triose and tetrose. The products from both substrates were similar with those described for the lichenases from *B. subtilis* (Huber and Nevin, 1977) and *R. succinogenes* (Erfle et al., 1988). From these results, the recombinant lichenase appears similar to other 1,3-1,4-β-D-glucanases in its general pattern of action, with a cleavage site which is a β-1,4 glucopyranosidic linkage of a 3-O-substituted β-D-glucopyranose unit (Buliga et al., 1986).

Lichenase and cellulase activities were detected using zymogram technology with an overlay containing lichenan or CMC, respectively. A clear strong band of lichenase activity was observed at approximately 27 kDa for the cell extract of the recombinant *E. coli*, the purified recombinant LICA, and the supernatant of Orpinomyces PC-2 culture. No activity was observed at this molecular weight when CMC was used as substrate, indicating that the LICA is specific for lichenan (FIG. 8). Additionally, the results revealed that the licA gene product was actively synthesized and secreted into medium of the Orpinomyces PC-2 culture. There were multiple faint high molecular mass bands in both Orpinomyces PC-2 and Neocallimastex EB 188 culture supernatant, which reflects cellulases having some ability to hydrolyze lichenan. No equivalent lichenase activity band corresponding to the Orpinomyces PC-2 lichenase was detected in the monocentric anaerobic fungus Neocallimastix EB 188 sample. Thus, Neocallimastix EB 188 appears to lack a lichenase gene.

1,3-1,4-β-D-Glucanases cleave 1,4-β-glycosidic linkages that are adjacent to 1,3-β-glycosidic linkages in mixed-linked glucans, which comprise an important component of plant hemicellulose. The present 1,3-1,4-β-D-glucanase (lichenase) does not cleave the β-1,4 glycosidic bonds in carboxymethylcellulose. To date, 1,3-1,4-β-D-glucanase has been found only in certain bacterial strains and in plants. This is believed to be the first report that describes the primary structure and properties of a typical β-1,3-1,4-D-glucanase from a fungus.

Most hydrolytic enzymes (particularly xylanases or cellulases) cloned from anaerobic fungi have a protein docking domain containing 2–3 repeated motifs of 30–40 amino acids each. The repeated peptide sequences are highly homologous to each other regardless of monocentric or polycentric origins. The repeated domains are not involved in catalysis or cellulose binding, but in formation of multi-enzyme complexes similar to the cellulosomes of anaerobic bacteria (Felex and Ljungdahl, 1993). Orpinomyces LICA does not contain a repeated peptide domain, which indicates that it is a free enzyme and not a component of the multienzyme complex. While 1,3-1,4-β-D-glucanases from the rumen bacteria R. flavefaciens (Flint et al., 1993) and *F. succinogenes* (Teather and Airflow, 1990) have a repeated docking domain, the partial sequence identities between the lichenases of the rumen bacteria and the present lichenase are much lower than those between the present lichenase and lichenases of Bacillus strains or *Clostridium thermocellum*.

Although the N-terminal signal sequence of LICA is a secretory signal that is functional both in *E. coli* and in Orpinomyces, the cleavage sites are different. Besides the difference between *E. coli* and eukaryotes with respect to signal peptides and proteases as discussed hereinabove, the different cleavage sites in LICA signal sequence may also relate to the cell membrane of the anaerobic fungi. Anaerobic fungi lack the ability to synthesize some common cell-membrane constituents such as sterol because of the absence of molecular oxygen. Instead, unusual lipids synthesized by the anaerobic pathway are incorporated into the anaerobic cell membrane (Kemp et al., 1984). In contrast, all previously described cloned hydrolytic enzyme genes in the fungi which contain the repeated peptide domain are neither effectively expressed nor secreted by *E. coli*. The expressed enzymes were also often subjected to extensive proteolysis in *E. coli*, perhaps due to partial removal of non-catalytic repeated domains of the enzymes (Gilbert et al., 1992; Fanutti et al., 1995).

Monocentric and polycentric anaerobic fungi are two different groups based on their morphological patterns. Very commonly, hydrolytic enzymes of monocentric Neocallimastex and Piromyces species have more than one catalytic domain in a single protein (Gilbert et al., 1992; Fanutti et al., 1995), but no such structure has been found in any cloned and sequenced genes for polycentric Orpinomyces hydrolytic enzymes so far. Neocallimastex EB 188 does not appear to have a lichenase with the same properties as the lichenase disclosed herein. Since cellulases also have activity to hydrolyze (1,4)-β bonds in lichenan and β-glucan, the selective advantage for Orpinomyces to synthesis lichenase in the rumen ecosystem is not clear.

The LICA signal peptide of this invention may be used to increase yield of foreign genes in host cells in which they are expressed. Any host cell in which the signal sequence is expressed and processed may be used. The signal peptide sequence (see SEQ ID NOs. 4 and 5 for coding and amino acid sequences) from the Aureobasidium xylanase can be substituted for the exemplified LICA signal sequence. Preferred host cells are Aureobasidium species and *S. cerevisiae*, as well as other yeasts known to the art for fermentation, including *Pichia pastoris* (Sreekrishna, K., "Strategies for optimizing protein expression and secretion in the methylotrophic yeast *Pichia pastoris*," in Baltz, R. H., et al. (eds.) Industrial Microorganisms: Basic and Applied Molecular Genetics, ASM Press, Washington, D.C. (1993) 119–126; Glick, B. R. and Pasternak, J. J., "Molecular Biotechnology—Principles and Applications of Recombinant DNA," ASM Press (1994) Washington, D.C.). Filamentous fungi such as Aspergillus, Trichoderma, Penicillium, etc. are also useful host organisms for expression of the DNA of this invention. (Van den Handel, et al., "Heterologous gene expression in filamentous fungi," (1991) In: Bennett, J. W. and Lasure, L. L. (eds.), More gene manipulations in fungi, Academy Press, Inc., New York, 397–428). When DNA encoding the LICA signal peptide is ligated to DNA encoding other proteins expressible in these hosts, the gene products are secreted from these organisms with the help of the signal peptide.

In addition the coding region for both the signal peptide and the mature LICA protein may be expressed in such hosts. Alternatively, the LICA mature protein coding region isolated from the signal sequence may be expressed in such hosts, or the coding region for the signal peptide isolated from the mature protein coding region may be expressed in such hosts.

In a preferred embodiment, vectors suitable for transformation of the host, preferably *S. cerevisiae*, with the licA gene, cDNA encoding the LICA mature protein, or the LICA signal peptide cDNA coding sequence (See SEQ ID NO:1–2) in combination with a suitable foreign gene expressible in *S. cerevisiae*, are prepared with the gene under control of a promoter expressible in the host, preferably *S. cerevisiae*. Preferably the promoter is a constitutive promoter such as the yeast enolase promoter (Sangadala et al., (1994) "Preparation and characterization of the site-directed E211Q mutant of yeast enolase," In: Abstracts of University System of Georgia 1994 Research Symposium: Advances in Biotechnology, Georgia State University, Atlanta, Ga., USA) or a strong inducible promoter such as the yeast alcohol dehydrogenase promoter (Pacitti, et al. (1994), "High level expression and purification of the enzymatically active cytoplasmic region of human CD45 phosphatase from yeast," Biochimica et Biophysica Acta 1222:277–286). The vector is used to transform the host either by integration into the chromosome or otherwise. The host organism is then cultured under conditions allowing expression of the gene and the product recovered from the culture medium.

Additionally, it will be recognized by those skilled in the art that allelic variations may occur in the licA coding sequence from different strains of Orpinomyces or other fungi which will not significantly change activity of the amino acid sequences of the proteins which these sequences encode. All such equivalent DNA sequences are included within the scope of this invention and the definition of the LICA mature protein coding region and signal sequence coding region. The skilled artisan understands that the amino acid sequence of the exemplified LICA polypeptide and signal peptide can be used to identify and isolate additional, nonexemplified nucleotide sequences which will encode functional equivalents to the polypeptides defined by the amino acid sequences given in SEQ ID NO:2, or an amino acid sequence of greater than 90% identity thereto and having equivalent biological activity. DNA sequences having at least about 70%, 80% and/or 85% homology to the DNA sequences of SEQ ID NO:1 (nucleotides 209 to 857) and encoding polypeptides with the same function are considered equivalent to the sequences of SEQ ID NO:1 and are included in the definition of "DNA encoding the LICA mature protein" and the "licA gene." Following the teachings herein, the skilled worker will be able to make a large number of operative embodiments having equivalent DNA sequences to those listed herein.

It is further understood that codons for conservative amino acid substitutions can change the primary amino acid sequence of a lichenase protein without significantly affecting the function of that protein. Such conservative amino acid substitutions are well known to the art (See, e.g., Dayhoff et al. (1978) in Atlas of Protein Sequence and Structure, Vol. 5, Supplement 3, Chapter 22, pages 345–352). Dayhoff et al.'s frequency tables are based on comparisons of amino acid sequences for proteins having the same function from a variety of evolutionarily different sources.

Percentage of sequence identity for polynucleotides and polypeptides is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by computerized implementations of known algorithms (e.g., GAP, BESTFIT, FASTA, and TFASTA in the Wisconsin Genetics Software Package, Genetics Computer Group (GCG), 575 Science Dr., Madison, Wis., or BlastN and BlastX available from the National Center for Biotechnology Information), or by inspection. Sequences are typically compared using either BlastN or BlastX with default parameters.

Substantial identity of polynucleotide sequences means that a polynucleotide comprises a sequence that has at least 75% sequence identity, preferably at least 80%, more preferably at least 90% and most preferably at least 95%. Typically, two polypeptides are considered to be substantially identical if at least 40%, preferably at least 60%, more preferably at least 90%, and most preferably at least 95% are identical or conservative substitutions. Sequences are preferably compared to a reference sequence using GAP using default parameters.

Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Another indication that polynucleotide sequences are substantially identical is if two molecules selectively hybridize to each other under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically stringent conditions for a Southern blot protocol involve washing at 65° C. with 0.2XSSC.

As used herein, a recombinant DNA molecule is not naturally occurring; it is produced by the hand of man in the laboratory. DNA segements or sequences from different sources can be joined by chemical synthesis, enzymatic ligation or by directed recombination.

Monoclonal or polyclonal antibodies, preferably monoclonal, specifically reacting with a lichenase encoded by a particular coding sequence may be made by methods known in the art. See, e.g., Harlow and Lane (1988) *Antibodies: A Laboratory Manual,* Cold Spring Harbor Laboratories; Goding (1986) *Monoclonal Antibodies: Principles and Practice,* 2d ed., Academic Press, New York.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning,* Second Edition, Cold Spring Harbor Laboratory, Plainview, N.Y.; Maniatis et al. (1982) *Molecular Cloning,* Cold Spring Harbor Laboratory, Plainview, N.Y.; Wu (ed.) (1993) *Meth. Enzymol.* 21, Part I; Wu (ed.) (1979) *Meth Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics,* Cold Spring Harbor Laboratory, Cold Spring Harbor, N.Y.; Old and Primrose (1981) *Principles of Gene Manipulation,* University of California Press, Berkeley; Schleif and Wensink (1982) *Practical Methods in Molecular Biology;* Glover (ed.) (1985) *DNA Cloning* Vol. I and II, IRL Press, Oxford, UK; Hames and Higgins (eds.) (1985) *Nucleic Acid Hybridization,* IRL Press, Oxford, UK; and Setlow and Hollaender (1979) *Genetic Engineering: Principles and Methods,* Vols. 1–4, Plenum Press, New York. Abbreviations and nomenclature, where employed, are deemed standard in the field and commonly used in professional journals such as those cited herein.

All references cited in the present application are incorporated by reference herein.

The following examples are provided for illustrative purposes, and are not intended to limit the scope of the invention as claimed herein. Any variations in the exemplified articles which occur to the skilled artisan are intended to fall within the scope of the present invention.

EXAMPLES

Example 1

Fungal Strain Culture Condition, and Vectors

Orpinomyces sp strain PC-2 was isolated and described by Bomeman et al. (1989); Neocallimastix sp. EB188 was provided by Dr. Calza (Washington State University). For enzyme production, the fungi were grown at 39° C. for 7 day in 2 L round bottles, each containing 1 L of basic medium (Barichievich and Calza, 1990) and 0.3% of coastal Bermudagrass (CBG). The medium was autoclaved for 30 min, and then cooled under a stream of $CO_2$. Penicillin (334 U/ml), streptomycin sulfate (80 $\mu$g/ml), and chloramphenicol (10 $\mu$g/ml) were filter sterilized (0.22 $\mu$m) (alt 230) and added to the stated final concentrations just prior to inoculation. *Escherichia coli* XL-Blue, $\lambda$ZAPII, pBluescript were products of Stratagene Cloning Systems (La Jolla, Calif.).

Example 2

Recovery of Extracellular, Periplasmic and Cellular 1,3-1,4-$\beta$-D-glucanase in Recombinant *E. coli*

Expression of endo-1,3-1,4-$\beta$-D-glucanase activity was detected according to the procedures of Neu and Heppel (1965) and Cornelis et al. (1982). *E. coli* was harvested by centrifugation at 3,200 g for 10 min (Beckman CS-6R). Cell free culture media were used for extracellular enzyme preparation. The cell pellet was washed twice in half the volume of the culture with 10 mM Tris-HCl pH 8.0 and suspended in the same volume of 25% sucrose 5 mM EDTA. The suspension was shaken for 10 min at room temperature. After centrifugation, the cells were suspended in the same volume of ice-cold water, and the suspension was shaken for 10 min at 4° C. After centrifugation, the supernatant was used as the periplasmic fraction. The cell pellet was sonicated to release intracellular 1,3-1,4-$\beta$-D-glucanase activity.

Example 3

Construction and Screening of an Orpinomyces cDNA Library

Extraction of RNA, purification of mRNA, and construction of a cDNA library from Orpinomyces PC-2 were described previously (Chen et al.,1995).

Top agar of NZY plates containing 5 mM isopropyl-1-thio-$\beta$-D-galactopyranoside (IPTG) and 0.2% lichenan (Sigma Chemical Co., St. Louis, Mo.) was used to isolate 1,3-1,4-β-D-glucanase-producing clones. After growth at 37° C. overnight, plates were stained by flooding with 0.1% Congo red for 20 min: clear haloes around colonies on the background indicate β-glucanase activity. Improved clear zones were obtained by treatment of stained agar plates with 1 M NaCl for 20 min. before observation. Pure positive clones were obtained after a secondary screening. Positive λ clones were converted to pBluescript SK—clones by in vivo excision. Single colonies were picked from the LB plates and separately inoculated into 5 ml LB+ampicillin (100 μg/ml) medium. The cultures were shaken for 7–8 hours at 250 rpm, 37° C. until the $OD_{600}$ of the cultures reached about 1.5, and then 10 μl of 0.5 M IPTG was added to each culture and the tubes were incubated for another 5 hours. The cultures were then sonicated. After centrifugation, the clear supernatants were used for testing lichenase and CMCase activities. The pBluescript DNAs were purified from overnight cultures in LB medium containing 50 μg/ml ampicillin using the Wizard™ Maxipreps plasmid purification system (Promega, Madison, Wis.). Nucleotide sequences of insert DNA were determined with an automatic PCR sequencer (Applied Biosystems Foster City, Calif.). Both universal and specific primers were used to sequence both strands of the inserts. Sequence data were analyzed using the Genetic Computer Group (GCG) version 8 (University of Wisconsin Biotechnology Center, Madison, Wis.) on the VAX/VMS system of the BioScience Computing Resource at the University of Georgia). The nucleotide sequence of licA of Orpinomyces sp. PC-2 has been assigned accession number U63813.

Example 4

Sodium Dodecyl Sulfate-Polyacrylamide Gel Electrophoresis (SDS-PAGE)

SDS-PAGE was carried out in Laernmli's buffer (Laemmli, U.K. (1970), *Nature* 227:680) with Coomassie brilliant blue R-250 (Sigma Chemical Co., St. Louis, Mo.). To visualize enzyme activity, samples were pretreated by incubating for 1 h at 40° C. in sample buffer and proteins were size-separated using SDS-PAGE at 4° C. To enhance removal of SDS and recovery of enzymatic activity following SDS-PAGE, gels were washed in 50 mM sodium citrate buffer, pH 6.0 with 1% (w/v) bovine serum albumin (BSA) (McGrew and Green, 1983).

Lichenase and CMCase activities were detected using the zymogram method of Beguin (1983) with a overlay containing 0.3% (w/v) lichenan or carboxymethylcellulose and agarose (2%, w/v) in 50 mM sodium citrate buffer, pH 6.0. The bands of enzyme activity were detected by staining the agarose gel with Congo red and destraining with 1 M NaCl.

Example 5

Enzyme Assay

All enzyme assays were carried out in duplicate in 50 mM sodium citrate buffer (pH 6.0) at 40° C. unless otherwise stated.

β-Glucanase activity was assayed by mixing a 0.2 ml aliquot of appropriately diluted enzyme with 0.4 ml buffer containing 0.4% (w/v) lichenan or barley β-glucan (Sigma Chemical Co., St. Louis, Mo.). The reaction was for 15 min and terminated by the addition 1.2 ml of 31 mM dinitrosalicylic acid (DNS) (Miller, 1959). The reaction tube was then placed in boiling water for 5 min before determining the absorbance at 550 nm. Glucose was used as standard. Activities on other polysaccharides were assayed in assays similar to that using lichenan.

One unit (U) of enzyme activity was defined as the amount of enzyme releasing one μmol glucose per min. Specific activity was expressed as units per mg of protein. Protein concentration was determined by the Bradford method and the Coomassie protein assay reagent (Pierce Chemical Co., Rockford, Ill.) in duplicate sets using BSA as standard.

Example 6

Enzyme Purification

An overnight culture (10 ml) of *E. coli* XL1-blue (pBluescript-licA) was inoculated into 500 ml LB-ampicillin (50 μg/ml) medium and grown to an $OD_{600}$ of 1.5 to 2.0. β-Glucanase expression was induced by the addition of 1 mM IPTG, and each culture was aerated for an additional 8 h at 37° C. A cell-free supernatant was obtained by centrifuging the culture at 4° C., 7,000×g for 10 min. The cell pellet was set aside, and the supernatant was concentrated to a volume of about 50 ml by using an ultrafiltration cell (Amicon Co., Beverly, Mass.) equipped with a PM 10 membrane. The concentrated supernatant was dialyzed against 500 ml of 20 mM potassium phosphate, pH 7.0. Ammonium sulfate was added to a concentration of 0.8 M. The solution was centrifuged at 4° C. and 20,000×g for 10 min to remove precipitated material. The clear solution was loaded on a Phenyl Superose 10/10 column (7.85 ml) equilibrated with 20 mM potassium phosphate, pH 7.0, containing 0.8 M ammonium sulphate. β-Glucanase was eluted with a 200 ml linear gradient of ammonium sulphate, from 0.8 to 0 M, then further with 100 ml distilled water. Fractions containing β-glucanase activity were pooled and concentrated, and the buffer was changed to 20 mM piperazine-HCl, pH 5.5. The solution was applied to a Mono Q 5/5 anion exchange column (1 ml) equilibrated with 20 mM piperazine-HCl buffer, pH 5.5. The β-glucanase fractions did not bind to the column, and the enzyme was eluted by applying 5 column volumes of the buffer. The β-glucanase-containing fractions were pooled and concentrated, and the buffer was changed to 20 mM sodium acetate, pH 5.0. The enzyme sample applied to a cation exchange Resource S column (1 ml). It did not adsorb to the column, and it was eluted out by further passing through 5 column volumes of the buffer. Final purification was achieved by gel filtration over Superdex 75 10/30 column (composite of cross-linked agarose and dextran gel filtration resin, Pharmacia, Piscataway, N.J.) equilibrated with 20 mM sodium phosphate, 100 mM NaCl, pH 6.0. Fractions exhibiting β-glucanase activity were combined and stored at −20° C.

For partial purification of native β-glucanase from the culture supernatant of Orpinomyces PC-2 culture, purification procedures as above were employed.

Example 7

N-Terminal Amino Acid Sequencing

Amino acid sequencing was done with protein bands isolated and purified after SDS-PAGE. The proteins were transferred onto a poly-vinylidene difluoride (PVDF) membrane in a Mini Trans-Blot cell (Bio-Rad Laboratories, Hercules, Calif.). The transferred proteins were visualized by Ponceau S staining and then excised with a razor blade. N-terminal amino acid sequencing was performed on an Applied Biosystems model 477A gas-phase sequencer equipped with an automatic on-line phenylthiohydantoin analyzer.

Example 8

Enzyme Characterization

The pH optimum was determined at 40° C. using the following buffers: 0.1 M sodium acetate (pH 4.2 to 5.4), sodium phosphate (pH 5.8 to 7.8), and Hepes-NaOH (pH 8.2 and 8.6) with increments of 0.4. Enzyme stability at different pH values was determined by measuring the residual activity after incubating the enzyme for 24 h at 4° C. at pH 3.0 to 10.2 (glycine-HCl buffer for pH 3.0 to 3.4; Hepes-NaOH for pH 9.0; piperazine-HC1 for pH 9.4 to 10.2). For other pH ranges, buffers were the same as those used for optimum pH determinations).

The effect of temperature on β-glucanase activity was determined by assaying the enzyme at temperatures from 30 to 65° C. with increments of 5° C. Thermostability was measured by incubating the enzyme in 50 mM sodium citrate buffer, pH 6.0 for 5 min to 24 h at temperatures from 40 to 60° C. with increments of 5° C. The enzyme solution was chilled in an ice bath for 5 min and then analyzed by running the standard assay at 40° C. In all these assays, lichenan was used as substrate.

For determination of $K_m$ and $V_{max}$, suitably diluted β-glucanase was incubated with lichenan and barley-β-glucan at concentrations ranging from 0.02 to 1.0% (w/v) under the assay conditions given. $K_m$ and $V_{max}$ values were obtained from Lineweaver-Burk plots.

Analysis of lichenan and barley-β-glucan degradation products was carried out with 5 U of the purified recombinant β-glucanase with 5 mg individual substrate in 1 ml of a 50 mM sodium citrate buffer, pH 6.0, at 40° C. Samples were periodically withdrawn and hydrolysis was stopped by placing the reaction in boiling water for 5 min. A 10 μl portion of each sample was spotted onto thin-layer chromatography (TLC) silica gel plate (Analtech, Inc., Newark, Del.) and chromatographed in a solvent system containing chloroform, glacial acetic acid, and water (6:7:1, vol/vol) (Lake and Goodwin, 1976). Plates were sprayed with a reagent consisting of aniline (2 ml), diphenylamine (2 g), acetone (100 ml), and 85% $H_3PO_4$ (15 ml). Then sugars were visualized by heating the plate for 15 min at 105° C. (Hansen, 1975). Glucose, cellobiose, cellotriose, cellotetraose and cellopentaose were used as standards.

TABLE 1

Homology comparison between Orpinomyces PC-2 LICA and other β-glucanases

| Strain | No. of AA overlap | Identity (%) |
|---|---|---|
| Bacillus polymyxa | 207 | 58 |
| Bacillus subtilis | 199 | 56.8 |
| Clostridium thermocellum | 243 | 52.7 |
| Bacillus macerans | 204 | 58.3 |
| Bacillus licheniformis | 200 | 57 |

TABLE 1-continued

Homology comparison between Orpinomyces PC-2 LICA and other β-glucanases

| Strain | No. of AA overlap | Identity (%) |
|---|---|---|
| Bacillus amyloliquefaciens | 200 | 55.5 |
| Clostridium thermocellum | 194 | 55.2 |
| Ruminococcus flavefaciens | 201 | 55.7 |
| Fibrobacter succinogenes | 170 | 30.6 |

TABLE 2

Summary of the purification of the recombinant LICA

| Step | Enzyme U | Specific activity U mg$^{-1}$ |
|---|---|---|
| Supernatant | 4,388 | 156.7 |
| Phenyl Superose | 3,149 | 1,850 |
| Mono Q | 2,648 | 2,400 |
| Resource S | 2,421 | 2,950 |
| Superdex 75 | 1,909 | 3,786 |

TABLE 3

Substrate specificity of purified recombinant LICA of Orpinomyces PC-2[a]

| Substrate | Linkage | Specific activity U mg$^{-1}$ | % |
|---|---|---|---|
| Lichenan | β-1,3; β-1,4 | 3,786 | 100 |
| Barley β-glucan | β-1,3; β-1,4 | 5,317 | 140 |
| Laminarin | β-1,3; β-1,6 | 0 | 0 |
| Pachyman | β-1,3 | 0 | 0 |
| CMC | β-1,4 | 0 | 0 |
| Acid swollen cellulose | β-1,4 | 0 | 0 |
| Pustulan | β-1,6 | 0 | 0 |

[a]The following substrates were not hydrolyzed: Avicel, arabinogalactan, mannan, araban, starch, xylan, pullulan, galactan, and Gum arabic (0.35% wt vol$^{-1}$), PNP-β-D-xyloside, PNP-β-D-glucoside, and PNP-β-D-cellobiose (1 mM).

TABLE 4

Nucleotide (SEQ ID NO:1) and deduced amino acid (SEQ ID NO:2) sequences of a β-1, 3-1, 4-glucanase (lichenase) cDNA (licA) of Orpinomyces PC-2

```
                                                 AATAAAAGAAAAAA

AAAATATATATTAAATAATAATATATATTAAAGTAAATAAAAAAAAATTTAAGAAAATAT

TTTCATTATATAATTAATATTTTTTGATAAAATAAAGATTATAATAAAATGAAAAGTATA
                                                          M  K  S  I

ATTTCTATTGCTGCTTTATCTGTTTTAGGATTGATTTCTAAAACTATGGCTGCTCCTGCT
 I  S  I  A  A  L  S  V  L  G  L  I  S  K  T  M  A  A  P  A
                                                        ↑
CCCGCTCCTGTTCCTGGTACTGCTTGGAATGGTAGTCATGATGTCATGGATTTCAACTAT
```

TABLE 4-continued

Nucleotide (SEQ ID NO:1) and deduced amino acid
(SEQ ID NO:2) sequences of a β-1, 3-1, 4-glucanase
(lichenase) cDNA (licA) of *Orpinomyces* PC-2

<u>P  A  P  V  P  G  T  A  W  N  G  S  H  D  V  M  D  F  N</u>  Y
         ↑
CATGAAAGTAACCGTTTTGAAATGTCAAACTGGCCAAATGGTGAAATGTTTAATTGTAGA
 H  E  S  N  R  F  E  M  S  N  W  P  N  G  E  M  F  N  C  R

TGGACTCCAAATAATGACAAATTTGAAAATGGTAAATTAAAGCTTACTATTGATAGAGAT
 W  T  P  N  N  D  K  F  E  N  G  K  L  K  L  T  I  D  R  D

GGTTCCGGATATACTTGTGGTGAATATCGTACTAAAAACTATTATGGATATGGTATGTTC
 G  S  G  Y  T  C  G  E  Y  R  T  K  N  Y  Y  G  Y  G  M  F

CAAGTTAATATGAAACCAATTAAGAATCCAGGAGTTGTTTCTTCCTTCTTTACTTACACA
 Q  V  N  M  K  P  I  K  N  P  G  V  V  S  S  F  F  T  Y  T

GGACCAAGTGATGGAACTAAGTGGGATGAAATTGATATAGAATTCCTTGGTTATGATACA
 G  P  S  D  G  T  K  W  D  E  I  D  I  E  F  L  G  Y  D  T

ACCAAAGTTCAATTTAACTACTACACTAATGGACAAGGTCATCATGAACATATTCATTAT
 T  K  V  Q  F  N  Y  Y  T  N  G  Q  G  H  H  E  H  I  H  Y

CTTGGATTTGATGCCTCTCAAGGATTCCATACCTATGGTTTCTTCTGGGCGAGAAATTCT
 L  G  F  D  A  S  Q  G  F  H  T  Y  G  F  F  W  A  R  N  S

ATTACATGGTATGTAGATGGTACAGCCGTTTACACTGCTTACGACAATATTCCAGATACA
 I  T  W  Y  V  D  G  T  A  V  Y  T  A  Y  D  N  I  P  D  T

CCAGGTAAGATTATGATGAATGCTTGGAATGGTATTGGAGTTGATGACTGGCTTAGACCA
 P  G  K  I  M  M  N  A  W  N  G  I  G  V  D  D  W  L  R  P

TTTAATGGAAGAACTAATATTAGTGCCTACTATGATTGGGTATCTTATGATGCACCAAGA
 F  N  G  R  T  N  I  S  A  Y  Y  D  W  V  S  Y  D  A  P  R

AACTAAATTATTTAAATAAATATATAATTTTTGTTTTAAAATTTAAAAAAAATATATATAT
 N  *
ATATATTATAAATTAATATGAAAAATAAAAATAAGATGT<u>AAAAAAAAAAAAAAAAAAA</u>

1. ↑: Cleavage site for the recombinant protein
2. Underline: n-terminal sequence of the recombinant protein
3. ↑: Cleavage site for the native protein from the fungus
4. Bold and underline: n-terminal sequence of native protein from the fungus
5. Double underline: poly-A tail

TABLE 5

Alignment of some homologous sequences with Oripinomyces LICA sequence

| | | |
|---|---|---|
| Lica_Orpin | 1 | ....MKSLISIAALSVLGISKTMAA...PAPAPVPGTAWNGSHDVMDFNYHKSNRFSMSK.WPNGKMFN |
| Gub_Bacpo | 1 | .MMKKKSWFTLMITGVISLFF.SVSAFA....GNVFWEPL.........SYFNSSTWOKADGYSNGQMFN |
| Gub_Bacsu | 1 | MPY.LKRVLLLLVTGIFMSLF.AVTATASAQTGGSFFDPF.........NGYNSGFWQKADGYSNGNMFN |
| Gub_Clotm | 1 | ...MKNRVISLLMASLLLVLSVIVAPFYKAEAATVVNTPFVA...VF.SNF.DSSQWEKAD.WAMGSVPM |
| Gub_Bacli | 1 | MSYRVKRMLMILVTGIFLSLE.TFAASASAQTSGSFYEPF.........NNYNTGLWQKKDGYSNGNMFN |
| Lami_Clotm | 1 | ...MKNRVISLLMASLLLVLSVIVAPFYKAEAATVVNTPFVT...VFRSNI.DSVQWKK.R.WAK..FVS |
| Gub_Fibsu | 1 | ...........................................................MN |
| | | |
| Lica_Orpin | 63 | CRNTPNNDKFEN.GKLKLTIDRDGSG...YTCGEYRTKNYGYGMFQVNMKPIKNPGVVSSFFTYTGPS. |
| Gub_Bacpo | 56 | CTWRANNVNFTNDGKLKLSDTS..PANNKYDCGEIRSTKNYGYGLYEVRMKPAKNTGIVSSFFTYTGPT. |
| Gub_Bacsu | 60 | CTWRANNVSMTSLGEMRLALTS..PTYNKFDCGENRSVQTYGYGLYEVRMKPAKNTGIVSSFFTYTGPT. |
| Gub_Clotm | 62 | CVWKPSQVTFSN.GKMILTLDREYGGSYPKSGEYRTKSFFGYGYYEVRMKAANVGIVSSFFTYTGPS. |
| Gub_Bacli | 61 | CTWRANNVSMTSLGEMRLSITS..PSYNKYDCGENRSVQTYGYCUYEVNMKPAKNVGIVSSFFTYTGPT. |
| Lami_Clotm | 60 | TVLEAFTGDISN.GKMILTLDRDYGGSYPKSGEYRTKSEFGYGYYEVRMKAANVGIVSSFFTYTGPS. |
| Gub_Fibsu | 3 | IKKTAVKSALA.VAAAAADTTEVSA.KDVSGAELYTLEEVQYGKFEARMMAAASGTVSSMFIYQNGSE |

TABLE 5-continued

Alignment of some homologous sequences with Oripinomyces LICA sequence

```
Lica_Orpin   128   ..DGTKWDEIDIEFLGYDTTKVQFNYYTNGQGHH...ESINYLGFDASQGFHTYGFFWARNSITWYVDGT
Gub_Bacpo    123   ..HGTQWDEIDIEFLGKDTTKVQFNYYTNGVGGH...EKIINLGFDASTSFHTYAFDWQPGYIKWYVDGV
Gub_Bacsu    127   ..DGTPWDEIDIEFLGKDTTKVQFNYYTNGAGNH...EKIVDLGFDAANAYHTYAFDWQPNSIKWYVDGQ
Gub_Clotm    130   ..DNNPWDEIDIEFLGKDTTKVQFNWYKNGVGGN...EYLHNLGFDASQDFHTYGFEWRPDYIDFYVDGK
Gub_Bacli    128   ..DGTPWDEIDIEFLGKDTTKVQFNYYTNGVGNH...EKIVNLGFDAANSYHTYAFDWQPNSIKWYVDGQ
Lami_Clotm   128   ..DNNPWDEIDIEFLGKDTTKVQFNWYKNGVGGN...EYLHNLGFDASQDFHTYGFEWRPDYIDFYVDGK
Gub_Fibsu     71   IADGRPWVSVDIEVLGKNPGSFQSNIITGKAGAQKTSEKHHAMSPAADQAFHTYGLEWIPNYVRWTVDGQ Lica_Orpin   193   AVYTA....YDNIPDTPGKIMMNAWNGIGVDDWLRPFNGRT.NISAYYDWYSYDAPRN*...........
Gub_Bacpo    188   LKHTA....TTNIPSTPGKIMMNLWNGTGVDSWLGSYNGAN.PIYAEYDWVKYTSN..............
Gub_Bacsu    192   LKHTA....TNQIPTTPGKIMMNLWNGTGVDEWLGSYNGAN.PLYAEYDWVKYTKK..............
Gub_Clotm    195   KYYRG....TRNIPVTPGKIMMNLWPGIGVDEWLGRYDGRT.PLQAEYEYVKYYPNGVPQDNPTPTPTIA
Gub_Bacli    193   LKHTA....TTQIPQTPGKIMMNLWNGAGVDEWLGSYNGVT.PLSRSLHWVRYTKR..............
Lami_Clotm   193   KYYRG....TRNIPVTPGKIMMNLWPGIGVDEWLGRYDGRT.PLQAEYGICKILS..............
Gub_Fibsu    141   ENRKTEGGQVSNLTGTQG.LRFNLWSSES.AANVGQFDESKLPLFQFINNWKVYKYTPGQGEGGSDFTLD Lica_Orpin          ....................(SEQ ID NO:2)
Gub_Bacpo           ....................(SEQ ID NO:7)
Gub_Bacsu           ....................(SEQ ID NO:8)
Gub_Clotm    260    PSTPTNPNLPLKGDVNGDGH (SEQ ID NO:9)
Gub_Bacli           ....................(SEQ ID NO:10)
Lami_Clotm          ....................(SEQ ID NO:11)
Gub_Fibsu    209    WTDNFDTFDGSRWGKGDWTF (SEQ ID NO:12)
```

REFERENCES CITED

Guliga, G. S., and Brant, D. A. (1986) Carbohydr. Res. 157, 139–156.

Fleming, M., and Kawami, K. (1977) Carbohydr. Res. 57, 15–23.

Anderson, M. A., and Stone, B. A. (1975) FEBS Lett. 52, 202–207.

Godfrey, T. (1983) Industrial Enzymology (Godfrey, T. & Reichelt, J., eds) p. 466, MacMillan, London.

White et al. (1983) Poult. Sci. 62, 853–862.

Murphy et al. (1984) Nucleic Acids Res. 12, 5355–5367.

Hofemeister et al. (1986) Gene (Amst.) 49, 177–187.

Borriss et al. (1990) Mol. Gen. Genet. 222, 278–283.

Lloberas et al. (1991) Eur. J. Biochem. 197, 337–343.

Louw et al. (1993) Appl. Microbiol. Biotechnol. 38, 507–513.

Gosalbes et al. (1991) J. Bacteriol. 173, 7705–7710.

Schimming et al. (1992) Eur. J. Biochem. 204, 13–19.

Teather, R., and Airflow, J. D. (1990) J. Bacteriol. 172, 3837–3841.

Flint et al. (1993) J. Bacteriol. 175, 2943–2951.

Becker et al. (1993) Mol. Gen. Genet. 238, 145–154.

Sakellaris et al. (1993) FEMS Microbiol. Lett. 109, 269–272.

Fincher et al. (1986) Proc. Natl. Acad. Sci. USA. 83, 2081–2085.

Zverlov, V. V. and Velikodvorskaya, G. A. (1990) Biotechnol. Lett. 12,811–816.

Orpin, C. G., and Joblin, K. N. (1988) in The Rumen Microbial Ecosystem, ed. Hobson, P. N. (Elsevier, London), pp. 129–151.

Akin et al. (1983) Appl. Environ. Microbiol. 46,738–748.

Barichievich, E. M., and R. E. Calza. (1990) Appl. Environ. Microbiol. 56:43–48.

Barr et al. (1989) Can. J. Bot. 67:2815–2824.

Bomeman et al. (1989) Appl. Environ. Microbiol. 55:1066–1073.

Breton et al. (1990) FEMS Microbiol. Lett. 70:177–182.

Chen et al. (1994) Appl. Environ. Microbiol. 60:64–70.

Chen et al. (1995) Proc. Acad. Sci. USA. 92,2587–2591.

Chen et al. (1995) in S. K. Ballal (ed.) SAAS Bulletin, Biochemistry and Biotechnolog 8:1–6.

Heath et al. (1983) Can. J. Bot. 61:295–307.

Ho, Y. W. and T. Bauchop (1990). Mycotaxon 38:397–405.

Miller, G. L. (1959) Anal. Chem. 31:426–428.

Orpin, G. C. (1975) J. Gen. Microbiol. 91:249–262.

Wubah, D. A. and M. S. Fuller (1991) Mycologia 83,303–310.

Laemmli, U. K. (1970) Nature (London) 227, 680–683.

McGrew, B. R. and Green, M. (1990) Anal. Biochem. 189, 68–74.

Beguin, P. (1983) Anal. Biochem. 131, 333–336.

Lake, B. D. and Goodwin, H. J. (1976) Chromatographic and electrophoretic techniques, vol. 1, p. 345–366. In I.Smith and J. M. T. Seakins (ed.), Lipids, 4th ed. Pitman Press, Bath, England.

Hansen, S. A. (1975) J. Chromatogr. 105:388–390.

Andersson, H. and von Heijne, G. (1991) Proc. Natl. Acad. Sci. USA 88:9751–9754.

Li et al. (1988) Proc. Natl. Acad. Sci. USA 85:7685–7689.

Kohara et al. (1991) J. Biol. Chem. 266, 20363–20368.

Von Heijne, G. (1986) Nucleic Acids Research 14, 11:4683–4690.

Airflow et al. (1988) Biochem. J. 255, 833–841.

Huber, D. J. and Nevin, D. J. (1977) Plant Physiol. 60, 300–304.

Buliga et al. (1986) Carbohydr. Res. 157,139–156.

Kemp et al. (1984) J. Gen. Microbiol. 130,27–37.

Neu, H. C. and Heppel, L. A. (1965) J. Biol. Chem. 240, 3685–3692.

Cornelis et al. (1982) Mol. Gen. Genet. 186, 507–511.

Juncosa et al. (1994) J. Biol. Chem. 269, 14530–14535.

Henrissat, B. and Bairoch, A. (1993) Biochem. J. 293, 781–788.

Gilbert et al. (1992) Mol. Microbiol. 6,2065–2072.

Denman et al. (1996) Appl. Environ. Microbiol. 62, 1889–1896.

Black et al. (1994) Biochem. J. 299, 381–387.

Zhou et al. (1994) Biochem. J. 297, 359–364.

What is claimed is:

1. A lichenase protein, said protein being purified from a fungus or a culture thereof or from a host cell transformed with a recombinant DNA molecule having a fungal lichenase coding sequence, wherein said lichenase has an amino acid sequence as given in SEQ ID NO:2 from amino acid 1 through amino acid 216 or a functionally equivalent sequence with at least about 70% amino acid sequence identity thereto, from amino acid −8 through amino acid 216 or a functionally equivalent sequence with at least about 70% amino acid sequence identity thereto or, from amino acid −29 through amino acid 216 or a functionally equivalent sequence with at least about 70% amino acid sequence identity thereto.

2. An isolated recombinant DNA molecule comprising a nucleotide sequence encoding a fungal lichenase of claim 1 wherein said lichenase has an amino acid sequence as given in SEQ ID NO:2 from amino acid 1 through amino acid 216 or a functionally equivalent sequence with at least about 70% identity thereto, from about amino acid −8 through amino acid 216 or a functionally equivalent sequence with at least about 70% identity thereto, or from about amino acid −29 through amino acid 216 or a functionally equivalent sequence with at least about 70% identity thereto.

3. The isolated recombinant DNA molecule of claim 2 wherein said lichenase is encoded by the nucleotide sequence as given in SEQ ID NO:1 from about nucleotide 210 through nucleotide 857 or a functionally equivalent sequence with at least about 70% identity thereto, from about nucleotide 186 through nucleotide 857 or a functionally equivalent sequence with at least about 70% identity thereto, or from nucleotide 123 through nucleotide 857 or a functionally equivalent sequence with at least about 70% identity thereto.

4. The isolated recombinant DNA molecule of claim 3 wherein the lichenase encoding nucleotide sequence is as given in SEQ ID NO;1 or a sequence having at least about 70% nucleotide sequence identity thereto and encoding a functional lichenase and additionally comprises DNA encoding a signal peptide immediately up stream of and operably linked to the nucleotide sequence encoding the mature lichenase protein.

5. The isolated recombinant DNA molecule of claim 4 wherein said signal peptide has an amino acid sequence as given in SEQ ID NO:5.

6. A host cell comprising the recombinant DNA molecule of claim 2, wherein said host cell is a member of a species selected from the group consisting of *Escherichia coli, Saccharomyces cerevisiae*, Aspergillus, Penicillium, *Trichoderma reesei*, Penicillium, Aureobasidium, Streptomyces and Bacillus.

7. The host cell of claim 6, wherein said recombinant DNA molecule comprises a nucleotide 20 sequence wherein said lichenase is encoded by the nucleotide sequence as given in SEQ ID NO:1 from nucleotide 210 through nucleotide 857 or a functionally equivalent sequence with at least about 70% identity thereto, from nucleotide 186 through nucleotide 857 or a functionally equivalent sequence with at least about 70% identity thereto, or from nucleotide 123 through nucleotide 857 or a functionally equivalent sequence with at least about 70% identity thereto.

8. The host cell of claim 6, wherein said recombinant DNA molecule comprises a nucleotide sequence as given in SEQ ID NO;1 or a sequence having at least about 70% nucleotide sequence identity thereto and encoding a functional lichenase, and additionally comprises DNA encoding a signal peptide immediately up stream of and operably linked to the nucleotide sequence encoding the mature lichenase protein.

9. A method of using the recombinant DNA molecule of claim 2 to produce a lichenase in a host cell other than Orpinomyces sp. strain PC-2, said method comprising the steps of:
 a) infecting or transforming said host cell capable of expressing a lichenase coding region with a vector comprising a promoter active in said host cell wherein said promoter is operably linked to the coding region for said lichenase, and
 b) culturing the infected or transformed host cell under conditions suitable for expression of said lichenase coding sequence.

10. The method of claim 9 wherein said host cell is selected from the group consisting of *Escherichia coli, Saccharomyces cerevisiae*, Asperigillus, Penicillium, *Trichoderma reesei*, Pichia, Streptomyces and Bacillus.

11. The method of claim 10 wherein said vector further comprises a nucleotide sequence encoding a signal peptide operably linked between said promoter and said coding region.

12. The method of claim 11 wherein said signal peptide has an amino acid sequence as given in SEQ ID NO:5.

13. The method of claim 9, wherein said lichenase has an amino acid sequence as given in SEQ ID NO:2, amino acids 1 to 216.

* * * * *

UNITED STATES PATENT AND TRADEMARK OFFICE
CERTIFICATE OF CORRECTION

PATENT NO. : 6,103,511
DATED : August 15, 2000
INVENTOR(S) : Li et al.

It is certified that error appears in the above-identified patent and that said Letters Patent is hereby corrected as shown below:

Other Publications:
In the Chen et al. (1997) reference, line 3, delete "Expresses" and replace with -- Expressed --.

Specification:

Column 2,
Line 67, delete "1=5-".

Column 3,
Line 9, delete "186" and replace with -- 185 --.
Line 10, delete "210" and replace with -- 209 --.

Column 4,
Line 51, delete "MRNA" and replace with -- mRNA --.
Line 57, delete "choses" and replace with -- chosen --.

Column 5,
Line 37, delete "xyn" and replace with -- XynA --.

Column 6,
Line 64, insert "(SEQ ID NO:2)" between "sequence" and "deduced".

Column 7,
Line 52, delete "=" at the beginning of the line.

Column 13,
Line 9, delete "SK----clones" and replace with -- SK-clones --.
Line 36, delete "Laernmli's" and replace with -- Laemmli's --.

Column 14,
Line 20, delete "supematant" and replace with -- supernatant --.

Columns 17, 18, 19, and 20,
Replace the entire Table 5 with attached Table 5.

UNITED STATES PATENT AND TRADEMARK OFFICE
CERTIFICATE OF CORRECTION

PATENT NO. : 6,103,511
DATED : August 15, 2000
INVENTOR(S) : Li et al.

It is certified that error appears in the above-identified patent and that said Letters Patent is hereby corrected as shown below:

CLAIMS:

Column 35,
Line 10, delete "210" and replace with -- 209 --.
Line 12, delete "186" and replace with -- 185 --.
Line 35, delete "20".

Signed and Sealed this

Seventh Day of August, 2001

*Attest:*

*Attesting Officer*

NICHOLAS P. GODICI
*Acting Director of the United States Patent and Trademark Office*

SEQUENCE LISTING

<160> NUMBER OF SEQ ID NOS: 12

<210> SEQ ID NO 1
<211> LENGTH: 972
<212> TYPE: DNA
<213> ORGANISM: Orpinomyces sp. PC-2
<220> FEATURE:
<221> NAME/KEY: LTR
<222> LOCATION: (186)..(857)
<220> FEATURE:
<221> NAME/KEY: CDS
<222> LOCATION: (123)..(857)
<220> FEATURE:
<221> NAME/KEY: mat_peptide
<222> LOCATION: (210)..(857)

<400> SEQUENCE: 1

```
aataaaagaa aaaaaaaata tatattaaat aataatatat attaaagtaa ataaaaaaaa      60
atttaagaaa atatttcat tatataatta atattttttg ataaaataaa gattataata      120 aa atg aaa agt ata att tct att gct gct tta tct gtt tta gga ttg        167
   Met Lys Ser Ile Ile Ser Ile Ala Ala Leu Ser Val Leu Gly Leu
              -25             -20             -15 att tct aaa act atg gct gct cct gct ccc gct cct gtt cct ggt act       215
Ile Ser Lys Thr Met Ala Ala Pro Ala Pro Ala Pro Val Pro Gly Thr
             -10              -5              -1   1 gct tgg aat ggt agt cat gat gtc atg gat ttc aac tat cat gaa agt       263
Ala Trp Asn Gly Ser His Asp Val Met Asp Phe Asn Tyr His Glu Ser
         5               10              15 aac cgt ttt gaa atg tca aac tgg cca aat ggt gaa atg ttt aat tgt       311
Asn Arg Phe Glu Met Ser Asn Trp Pro Asn Gly Glu Met Phe Asn Cys
 20              25              30 aga tgg act cca aat aat gac aaa ttt gaa aat ggt aaa tta aag ctt       359
Arg Trp Thr Pro Asn Asn Asp Lys Phe Glu Asn Gly Lys Leu Lys Leu
 35              40              45              50 act att gat aga gat ggt tcc gga tat act tgt ggt gaa tat cgt act       407
Thr Ile Asp Arg Asp Gly Ser Gly Tyr Thr Cys Gly Glu Tyr Arg Thr
             55              60              65 aaa aac tat tat gga tat ggt atg ttc caa gtt aat atg aaa cca att       455
Lys Asn Tyr Tyr Gly Tyr Gly Met Phe Gln Val Asn Met Lys Pro Ile
         70              75              80 aag aat cca gga gtt gtt tct tcc ttc ttt act tac aca gga cca agt       503
Lys Asn Pro Gly Val Val Ser Ser Phe Phe Thr Tyr Thr Gly Pro Ser
         85              90              95 gat gga act aag tgg gat gaa att gat ata gaa ttc ctt ggt tat gat       551
Asp Gly Thr Lys Trp Asp Glu Ile Asp Ile Glu Phe Leu Gly Tyr Asp
100             105             110 aca acc aaa gtt caa ttt aac tac tac act aat gga caa ggt cat cat       599
Thr Thr Lys Val Gln Phe Asn Tyr Tyr Thr Asn Gly Gln Gly His His
115             120             125             130 gaa cat att cat tat ctt gga ttt gat gcc tct caa gga ttc cat acc       647
Glu His Ile His Tyr Leu Gly Phe Asp Ala Ser Gln Gly Phe His Thr
             135             140             145 tat ggt ttc ttc tgg gcg aga aat tct att aca tgg tat gta gat ggt       695
Tyr Gly Phe Phe Trp Ala Arg Asn Ser Ile Thr Trp Tyr Val Asp Gly
         150             155             160 aca gcc gtt tac act gct tac gac aat att cca gat aca cca ggt aag       743
Thr Ala Val Tyr Thr Ala Tyr Asp Asn Ile Pro Asp Thr Pro Gly Lys
         165             170             175 att atg atg aat gct tgg aat ggt att gga gtt gat gac tgg ctt aga       791
Ile Met Met Asn Ala Trp Asn Gly Ile Gly Val Asp Asp Trp Leu Arg
```

-continued

```
              180                 185                 190
cca ttt aat gga aga act aat att agt gcc tac tat gat tgg gta tct      839
Pro Phe Asn Gly Arg Thr Asn Ile Ser Ala Tyr Tyr Asp Trp Val Ser
195                 200                 205                 210 tat gat gca cca aga aac taaattattt aaataaatat ataattttg              887
Tyr Asp Ala Pro Arg Asn
                215 ttttaaaatt taaaaaata tatatatata tattataaat taatatgaaa aataaaaata     947 agatgtaaaa aaaaaaaaaa aaaad                                          972
```

<210> SEQ ID NO 2
<211> LENGTH: 245
<212> TYPE: PRT
<213> ORGANISM: Orpinomyces sp. PC-2

<400> SEQUENCE: 2

```
Met Lys Ser Ile Ile Ser Ile Ala Ala Leu Ser Val Leu Gly Leu Ile
                -25                 -20                 -15

Ser Lys Thr Met Ala Ala Pro Ala Pro Ala Pro Val Pro Gly Thr Ala
            -10                  -5              -1    1

Trp Asn Gly Ser His Asp Val Met Asp Phe Asn Tyr His Glu Ser Asn
      5                  10                  15

Arg Phe Glu Met Ser Asn Trp Pro Asn Gly Glu Met Phe Asn Cys Arg
 20                  25                  30                  35

Trp Thr Pro Asn Asn Asp Lys Phe Glu Asn Gly Lys Leu Lys Leu Thr
                 40                  45                  50

Ile Asp Arg Asp Gly Ser Gly Tyr Thr Cys Gly Glu Tyr Arg Thr Lys
             55                  60                  65

Asn Tyr Tyr Gly Tyr Gly Met Phe Gln Val Asn Met Lys Pro Ile Lys
         70                  75                  80

Asn Pro Gly Val Val Ser Ser Phe Phe Thr Tyr Thr Gly Pro Ser Asp
     85                  90                  95

Gly Thr Lys Trp Asp Glu Ile Asp Ile Glu Phe Leu Gly Tyr Asp Thr
100                 105                 110                 115

Thr Lys Val Gln Phe Asn Tyr Tyr Thr Asn Gly Gln Gly His His Glu
                120                 125                 130

His Ile His Tyr Leu Gly Phe Asp Ala Ser Gln Gly Phe His Thr Tyr
            135                 140                 145

Gly Phe Pro Trp Ala Arg Asn Ser Ile Thr Trp Tyr Val Asp Gly Thr
        150                 155                 160

Ala Val Tyr Thr Ala Tyr Asp Asn Ile Pro Asp Thr Pro Gly Lys Ile
    165                 170                 175

Met Met Asn Ala Trp Asn Gly Ile Gly Val Asp Asp Trp Leu Arg Pro
180                 185                 190                 195

Phe Asn Gly Arg Thr Asn Ile Ser Ala Tyr Tyr Asp Trp Val Ser Tyr
                200                 205                 210

Asp Ala Pro Arg Asn
            215
```

<210> SEQ ID NO 3
<211> LENGTH: 12
<212> TYPE: PRT
<213> ORGANISM: Orpinomyces sp. PC-2

<400> SEQUENCE: 3

Gly Thr Ala Trp Asn Gly Leu His Asp Val Met Asp

-continued

```
                1               5                  10

<210> SEQ ID NO 4
<211> LENGTH: 102
<212> TYPE: DNA
<213> ORGANISM: Aureobasidium pullulans
<220> FEATURE:
<221> NAME/KEY: CDS
<222> LOCATION: (1)..(102)

<400> SEQUENCE: 4 atg aag ttc ttc gcc acc att gct gct ctc gtt gtg gga gct gtt gct     48
Met Lys Phe Phe Ala Thr Ile Ala Ala Leu Val Val Gly Ala Val Ala
 1               5                  10                  15 gcc cca gtc gca gag gct gag gct gag gcc agc agc ccc atg ctg atc     96
Ala Pro Val Ala Glu Ala Glu Ala Glu Ala Ser Ser Pro Met Leu Ile
                20                  25                  30 gaa cgt                                                             102
Glu Arg

<210> SEQ ID NO 5
<211> LENGTH: 34
<212> TYPE: PRT
<213> ORGANISM: Aureobasidium pullulans

<400> SEQUENCE: 5

Met Lys Phe Phe Ala Thr Ile Ala Ala Leu Val Val Gly Ala Val Ala
 1               5                  10                  15

Ala Pro Val Ala Glu Ala Glu Ala Glu Ala Ser Ser Pro Met Leu Ile
                20                  25                  30

Glu Arg

<210> SEQ ID NO 6
<211> LENGTH: 5
<212> TYPE: PRT
<213> ORGANISM: Orpinomyces sp. PC-2

<400> SEQUENCE: 6

Asp Glu Ile Asp Ile
 1               5

<210> SEQ ID NO 7
<211> LENGTH: 238
<212> TYPE: PRT
<213> ORGANISM: Bacillus polymyxa

<400> SEQUENCE: 7

Met Met Lys Lys Lys Ser Trp Phe Thr Leu Met Ile Thr Gly Val Ile
 1               5                  10                  15

Ser Leu Phe Phe Ser Val Ser Ala Phe Ala Gly Asn Val Phe Trp Glu
                20                  25                  30

Pro Leu Ser Tyr Phe Asn Ser Ser Thr Trp Gln Lys Ala Asp Gly Tyr
            35                  40                  45

Ser Asn Gly Gln Met Phe Asn Cys Thr Trp Arg Ala Asn Asn Val Asn
        50                  55                  60

Phe Thr Asn Asp Gly Lys Leu Lys Leu Ser Leu Thr Ser Pro Ala Asn
 65                 70                  75                  80

Asn Lys Phe Asp Cys Gly Glu Tyr Arg Ser Thr Asn Asn Tyr Gly Tyr
                85                  90                  95

Gly Leu Tyr Glu Val Ser Met Lys Pro Ala Lys Asn Thr Gly Ile Val
            100                 105                 110
```

```
Ser Ser Phe Phe Thr Tyr Thr Gly Pro Ser His Gly Thr Gln Trp Asp
        115                 120                 125
Glu Ile Asp Ile Glu Phe Leu Gly Lys Asp Thr Thr Lys Val Gln Phe
130                 135                 140
Asn Tyr Tyr Thr Asn Gly Val Gly His Glu Lys Ile Ile Asn Leu
145                 150                 155                 160
Gly Phe Asp Ala Ser Thr Ser Phe His Thr Tyr Ala Phe Asp Trp Gln
                165                 170                 175
Pro Gly Tyr Ile Lys Trp Tyr Val Asp Gly Val Leu Lys His Thr Ala
                180                 185                 190
Thr Thr Asn Ile Pro Ser Thr Pro Gly Lys Ile Met Met Asn Leu Trp
                195                 200                 205
Asn Gly Thr Gly Val Asp Ser Trp Leu Gly Ser Tyr Asn Gly Ala Asn
210                 215                 220
Pro Leu Tyr Ala Glu Tyr Asp Trp Val Lys Tyr Thr Ser Asn
225                 230                 235

<210> SEQ ID NO 8
<211> LENGTH: 242
<212> TYPE: PRT
<213> ORGANISM: Bacillus subtilis

<400> SEQUENCE: 8

Met Pro Tyr Leu Lys Arg Val Leu Leu Leu Val Thr Gly Leu Phe
  1                 5                  10                  15
Met Ser Leu Phe Ala Val Thr Ala Thr Ala Ser Ala Gln Thr Gly Gly
                 20                  25                  30
Ser Phe Phe Asp Pro Phe Asn Gly Tyr Asn Ser Gly Phe Trp Gln Lys
                 35                  40                  45
Ala Asp Gly Tyr Ser Asn Gly Asn Met Phe Asn Cys Thr Trp Arg Ala
 50                  55                  60
Asn Asn Val Ser Met Thr Ser Leu Gly Glu Met Arg Leu Ala Leu Thr
 65                  70                  75                  80
Ser Pro Ala Tyr Asn Lys Phe Asp Cys Gly Glu Asn Arg Ser Val Gln
                 85                  90                  95
Thr Tyr Gly Tyr Gly Leu Tyr Glu Val Arg Met Lys Pro Ala Lys Asn
                100                 105                 110
Thr Gly Ile Val Ser Ser Phe Phe Thr Tyr Thr Gly Pro Thr Asp Gly
                115                 120                 125
Thr Pro Trp Asp Glu Ile Asp Ile Glu Phe Leu Gly Lys Asp Thr Thr
                130                 135                 140
Lys Val Gln Phe Asn Tyr Tyr Thr Asn Gly Ala Gly Asn His Glu Lys
145                 150                 155                 160
Ile Val Asp Leu Gly Phe Asp Ala Ala Asn Ala Tyr His Thr Tyr Ala
                165                 170                 175
Phe Asp Trp Gln Pro Asn Ser Ile Lys Trp Tyr Val Asp Gly Gln Leu
                180                 185                 190
Lys His Thr Ala Thr Asn Gln Ile Pro Thr Thr Pro Gly Lys Ile Met
                195                 200                 205
Met Asn Leu Trp Asn Gly Thr Gly Val Asp Glu Trp Leu Gly Ser Tyr
                210                 215                 220
Asn Gly Val Asn Pro Leu Tyr Ala His Tyr Asp Trp Val Arg Tyr Thr
225                 230                 235                 240
Lys Lys
```

<210> SEQ ID NO 9
<211> LENGTH: 279
<212> TYPE: PRT
<213> ORGANISM: Clostridium thermocellum

<400> SEQUENCE: 9

Met Lys Asn Arg Val Ile Ser Leu Leu Met Ala Ser Leu Leu Leu Val
1               5                   10                  15

Leu Ser Val Ile Val Ala Pro Phe Tyr Lys Ala Glu Ala Ala Thr Val
            20                  25                  30

Val Asn Thr Pro Phe Val Ala Val Phe Ser Asn Phe Asp Ser Ser Gln
        35                  40                  45

Trp Glu Lys Ala Asp Trp Ala Asn Gly Ser Val Phe Asn Cys Val Trp
    50                  55                  60

Lys Pro Ser Gln Val Thr Phe Ser Asn Gly Lys Met Ile Leu Thr Leu
65                  70                  75                  80

Asp Arg Glu Tyr Gly Gly Ser Tyr Pro Tyr Lys Ser Gly Glu Tyr Arg
                85                  90                  95

Thr Lys Ser Phe Phe Gly Tyr Gly Tyr Tyr Glu Val Arg Met Lys Ala
            100                 105                 110

Ala Lys Asn Val Gly Ile Val Ser Ser Phe Phe Thr Tyr Thr Gly Pro
        115                 120                 125

Ser Asp Asn Asn Pro Trp Asp Glu Ile Asp Ile Glu Phe Leu Gly Lys
    130                 135                 140

Asp Thr Thr Lys Val Gln Phe Asn Trp Tyr Lys Asn Gly Val Gly Gly
145                 150                 155                 160

Asn Glu Tyr Leu His Asn Leu Gly Phe Asp Ala Ser Gln Asp Phe His
                165                 170                 175

Thr Tyr Gly Phe Glu Trp Arg Pro Asp Tyr Ile Asp Phe Tyr Val Asp
            180                 185                 190

Gly Lys Lys Val Tyr Arg Gly Thr Arg Asn Ile Pro Val Thr Pro Gly
        195                 200                 205

Lys Ile Met Met Asn Leu Trp Pro Gly Ile Gly Val Asp Glu Trp Leu
    210                 215                 220

Gly Arg Tyr Asp Gly Arg Thr Pro Leu Gln Ala Glu Tyr Glu Tyr Val
225                 230                 235                 240

Lys Tyr Tyr Pro Asn Gly Val Pro Gln Asp Asn Pro Thr Pro Thr Pro
                245                 250                 255

Thr Ile Ala Pro Ser Thr Pro Thr Asn Pro Asn Leu Pro Leu Lys Gly
            260                 265                 270

Asp Val Asn Gly Asp Gly His
        275

<210> SEQ ID NO 10
<211> LENGTH: 243
<212> TYPE: PRT
<213> ORGANISM: Bacillus licheniformis

<400> SEQUENCE: 10

Met Ser Tyr Arg Val Lys Arg Met Leu Met Leu Leu Val Thr Gly Leu
1               5                   10                  15

Phe Leu Ser Leu Ser Thr Phe Ala Ala Ser Ala Ser Ala Gln Thr Gly
            20                  25                  30

Gly Ser Phe Tyr Glu Pro Phe Asn Asn Tyr Asn Thr Gly Leu Trp Gln
        35                  40                  45

```
Lys Ala Asp Gly Tyr Ser Asn Gly Asn Met Phe Asn Cys Thr Trp Arg
     50                  55                  60

Ala Asn Asn Val Ser Met Thr Ser Leu Gly Glu Met Arg Leu Ser Leu
 65                  70                  75                  80

Thr Ser Pro Ser Tyr Asn Lys Phe Asp Cys Gly Glu Asn Arg Ser Val
                 85                  90                  95

Gln Thr Tyr Gly Tyr Gly Leu Tyr Glu Val Asn Met Lys Pro Ala Lys
                100                 105                 110

Asn Val Gly Ile Val Ser Ser Phe Phe Thr Tyr Thr Gly Pro Thr Asp
            115                 120                 125

Gly Thr Pro Trp Asp Glu Ile Asp Ile Glu Phe Leu Gly Lys Asp Thr
130                 135                 140

Thr Lys Val Gln Phe Asn Tyr Tyr Thr Asn Gly Val Gly Asn His Glu
145                 150                 155                 160

Lys Ile Val Asn Leu Gly Phe Asp Ala Ala Asn Ser Tyr His Thr Tyr
                165                 170                 175

Ala Phe Asp Trp Gln Pro Asn Ser Ile Lys Trp Tyr Val Asp Gly Gln
            180                 185                 190

Leu Lys His Thr Ala Thr Thr Gln Ile Pro Gln Thr Pro Gly Lys Ile
        195                 200                 205

Met Met Asn Leu Trp Asn Gly Ala Gly Val Asp Glu Trp Leu Gly Ser
    210                 215                 220

Tyr Asn Gly Val Thr Pro Leu Ser Arg Ser Leu His Trp Val Arg Tyr
225                 230                 235                 240

Thr Lys Arg

<210> SEQ ID NO 11
<211> LENGTH: 242
<212> TYPE: PRT
<213> ORGANISM: Clostridium thermocellum

<400> SEQUENCE: 11

Met Lys Asn Arg Val Ile Ser Leu Leu Met Ala Ser Leu Leu Leu Val
 1               5                  10                  15

Leu Ser Val Ile Val Ala Pro Phe Tyr Lys Ala Glu Ala Ala Thr Val
                20                  25                  30

Val Asn Thr Pro Phe Val Ala Val Phe Arg Ser Asn Phe Asp Ser Val
            35                  40                  45

Gln Trp Lys Lys Arg Trp Ala Lys Phe Val Ser Thr Val Leu Glu Ala
     50                  55                  60

Phe Thr Gly Asp Ile Ser Asn Gly Lys Met Ile Leu Thr Leu Asp Arg
 65                  70                  75                  80

Glu Tyr Gly Gly Ser Tyr Pro Tyr Lys Ser Gly Glu Tyr Arg Thr Lys
                 85                  90                  95

Ser Phe Phe Gly Tyr Gly Tyr Glu Val Arg Met Lys Ala Ala Lys
                100                 105                 110

Asn Val Gly Ile Val Ser Ser Phe Phe Thr Tyr Thr Gly Pro Ser Asp
            115                 120                 125

Asn Asn Pro Trp Asp Glu Ile Asp Ile Glu Phe Leu Gly Lys Asp Thr
130                 135                 140

Thr Lys Val Gln Phe Asn Trp Tyr Lys Asn Gly Val Gly Gly Asn Glu
145                 150                 155                 160

Tyr Leu His Asn Leu Gly Phe Asp Ala Ser Gln Asp Phe His Thr Tyr
                165                 170                 175
```

```
Gly Phe Glu Trp Arg Pro Asp Tyr Ile Asp Phe Tyr Val Asp Gly Lys
            180                 185                 190

Lys Val Tyr Arg Gly Thr Arg Asn Ile Pro Val Thr Pro Gly Lys Ile
        195                 200                 205

Met Met Asn Leu Trp Pro Gly Ile Gly Val Asp Glu Trp Leu Gly Arg
        210                 215                 220

Tyr Asp Gly Arg Thr Pro Leu Gln Ala Glu Tyr Gly Ile Cys Lys Ile
225                 230                 235                 240

Leu Ser

<210> SEQ ID NO 12
<211> LENGTH: 228
<212> TYPE: PRT
<213> ORGANISM: Fibrobacter succinogenes

<400> SEQUENCE: 12

Met Asn Ile Lys Lys Thr Ala Val Lys Ser Ala Leu Ala Val Ala Ala
  1               5                  10                  15

Ala Ala Ala Ala Leu Thr Thr Asn Val Ser Ala Lys Asp Phe Ser Gly
                20                  25                  30

Ala Glu Leu Tyr Thr Leu Glu Glu Val Gln Tyr Gly Lys Phe Glu Ala
            35                  40                  45

Arg Met Lys Met Ala Ala Ser Gly Thr Val Ser Ser Met Phe Leu
    50                  55                  60

Tyr Gln Asn Gly Ser Glu Ile Ala Asp Gly Arg Pro Trp Val Glu Val
 65                 70                  75                  80

Asp Ile Glu Val Leu Gly Lys Asn Pro Gly Ser Phe Gln Ser Asn Ile
                85                  90                  95

Ile Thr Gly Lys Ala Gly Ala Gln Lys Thr Ser Glu Lys His His Ala
                100                 105                 110

Val Ser Pro Ala Ala Asp Gln Ala Phe His Thr Tyr Gly Leu Glu Trp
            115                 120                 125

Thr Pro Asn Tyr Val Arg Trp Thr Val Asp Gly Gln Glu Val Arg Lys
        130                 135                 140

Thr Glu Gly Gly Gln Val Ser Asn Leu Thr Gly Thr Gln Gly Leu Arg
145                 150                 155                 160

Phe Asn Leu Trp Ser Ser Glu Ser Ala Ala Trp Val Gly Gln Phe Asp
                165                 170                 175

Glu Ser Lys Leu Pro Leu Phe Gln Phe Ile Asn Trp Val Lys Val Tyr
            180                 185                 190

Lys Tyr Thr Pro Gly Gln Gly Glu Gly Gly Ser Asp Phe Thr Leu Asp
        195                 200                 205

Trp Thr Asp Asn Phe Asp Thr Phe Asp Gly Ser Arg Trp Gly Lys Gly
        210                 215                 220

Asp Trp Thr Phe
225
```